US007575750B2

(12) United States Patent
Xie et al.

(10) Patent No.: US 7,575,750 B2
(45) Date of Patent: Aug. 18, 2009

(54) HUMAN IMMUNODEFICIENCY VIRUS (HIV) GP41 PEPTIDE DERIVATIVES WITH ENHANCED SOLUBILITY AND ANTIVIRAL ACTIVITY

(75) Inventors: Dong Xie, Germantown, MD (US); He Jiang, Rockville, MD (US)

(73) Assignee: Frontiers Biotechnologies Col, Ltd., Chongqing (CN)

( * ) Notice: Subject to any disclaimer, the term of this patent is extended or adjusted under 35 U.S.C. 154(b) by 824 days.

(21) Appl. No.: 10/667,966

(22) Filed: Sep. 23, 2003

(65) Prior Publication Data

US 2005/0089840 A1 Apr. 28, 2005

Related U.S. Application Data

(60) Provisional application No. 60/412,797, filed on Sep. 24, 2002.

(51) Int. Cl.
*A61K 39/385* (2006.01)
*A61K 39/21* (2006.01)

(52) U.S. Cl. ................................ 424/196.11; 424/188.1

(58) Field of Classification Search .............. 424/188.1, 424/208.1

See application file for complete search history.

(56) References Cited

U.S. PATENT DOCUMENTS

| | | | | |
|---|---|---|---|---|
| 3,719,667 | A | 3/1973 | Gutowski | |
| 3,840,556 | A | 10/1974 | Kukolja | |
| 5,612,034 | A | 3/1997 | Pouletty et al. | |
| 5,840,697 | A | 11/1998 | Blondelle et al. | |
| 6,258,782 | B1 * | 7/2001 | Barney et al. | 514/13 |
| 6,268,479 | B1 | 7/2001 | Stern et al. | |
| 6,281,331 | B1 | 8/2001 | Kang et al. | |

FOREIGN PATENT DOCUMENTS

| | | | |
|---|---|---|---|
| WO | WO 99/59615 | * | 11/1999 |
| WO | WO 00/69902 | * | 5/2000 |
| WO | WO 00/69902 | | 11/2000 |
| WO | WO 00/69911 | * | 11/2000 |
| WO | WO 00/70665 | | 11/2000 |

OTHER PUBLICATIONS

T.W. Green, "*Protection for the Carboxyl Group*," Chapter 5, Protective Groups in Organic Synthesis, published by John Wiley & Sons, New York, USA, 1981, pp. 152-192.

Creamer et al., "*α-Helix-Forming Propensities in Peptides and Proteins*," Proteins: Structure, Function, and Genetics 19:85-97 (1994), Wiley-Liss, Inc.

Chan et al., "*Evidence that a prominent cavity in the coiled coil of HIV type 1 gp41 is an attractive drug target,*" Proc. Natl. Acad. Sci. USA, vol. 95, pp. 15613-15617, Dec. 1998, The National Academy of Sciences.

Malashkevich et al., "*Crystal structure of the simian immunodeficiency virus (SIV) gp41 core: Conserved helical interactions underlie the broad inhibitory activity of gp41 peptides*," Proc. Natl. Acad. Sci USA, vol. 95, pp. 9134-9139, Aug. 1998, The National Academy of Sciences.

Wild et al., "*Peptides corresponding to a predictive α-helical domain of human immunodeficiency virus type 1 gp41 are potent inhibitors of virus infection*," Proc. Natl. Acad. Sci. USA, vol. 91, pp. 9770-9774, Oct. 1994, The National Academy of Sciences.

Stehle et al., "*The loading rate determines tumor targeting properties of methotrexate-albumin conjugates in rats*," Anti-Cancer Drugs, 1997, vol. 8, pp. 677-685, Rapid Science Publishers.

* cited by examiner

*Primary Examiner*—J. S. Parkin
(74) *Attorney, Agent, or Firm*—Hunton & Williams LLP

(57) ABSTRACT

This invention relates to gp41 peptide derivatives that are inhibitors of viral infection and/or exhibit antifusogenic properties. In particular, this invention relates to gp41 derivatives having inhibiting activity against human immunodeficiency virus (HIV) and simian immunodeficiency virus (SIV) with enhanced duration of action for the treatment of the respective viral infections.

3 Claims, 1 Drawing Sheet

Figure 1

Sequences showing helix-forming heptads:

| | | | | | | | | | | |
|---|---|---|---|---|---|---|---|---|---|---|
| T-20 | | | YTSL | IHSLIEE | SQNQQEK | NEQELLE | LDKWASL | WNWF | | (SEQ ID NO:4) |
| **T-1249** | | | WQEWEQK | ITALLEQ | AQIQQEK | NEYELQK | LDKWASL | WEWF | | (SEQ ID NO:3) |
| C-34 | | WMEWDRE | INNYTSL | IHSLIEE | SQNQQEK | NEQELL | | | | (SEQ ID NO:5) |
| SIV C34 | | WQEWERK | VDFLEEN | ITALLEE | AQIQQEK | NMYELQ | | | | (SEQ ID NO:6) |
| FB005 | **S LEQIWNNMT** | W**E**EWDRE | INNYT**E**L | IHELIEE | SQNQQEK | NEQELL | | | | (SEQ ID NO:1) |
| FB006 | | W**E**EWDRE | INNYT**K**L | IHELIEE | SQNQQEK | NEQELL | | | | (SEQ ID NO:2) |
| FB066 | | W**E**EWDRE | INNYT**K**L | IHELIEE | SQNQQE**E** | NEQELL | | | | (SEQ ID NO:7) |
| FB005M | S LEQIWNNMT | WEEWDRE | INNYT**X**L | IHELIEE | SQNQQEK | NEQELL | | | | (SEQ ID NO:8) |
| FB005CM | S LEQIWNNMT | WEEWDRE | INNYTEL | IHELIEE | SQNQQEK | NEQELL**X** | | | | (SEQ ID NO:9) |
| FB006M | | WEEWDRE | INNYT**X**L | IHELIEE | SQNQQEK | NEWELL | | | | (SEQ ID NO:10) |
| FB007M | | WEEWDRE | INNYTEL | IHELIEE | SQNQQEK | NEQELL**X** | | | | (SEQ ID NO:11) |
| FB066M | | W**E**EWDRE | INNYT**X**L | IH**E**LIEE | SQNQQE**E** | NEQELL | | | | (SEQ ID NO:14) |
| FB066KM | | W**E**EWDRE | INNYT**K**L | IH**E**LIEE | SQNQQE**E** | NEQELL**X** | | | | (SEQ ID NO:15) |
| FB010M | | | WQEWEQK | ITALL**X**Q | AQIQQEK | NEYELQK | LDKWASL | WEWF | | (SEQ ID NO:12) |
| FB010KM | | | WQEWEQK | ITALIEQ | AQIQQEK | NEYELQK | LDKWASL | WEWF**X** | | (SEQ ID NO:13) |

(X in the above formulae is a lysine residue derivatized with a maleimide linking moiety)

HUMAN IMMUNODEFICIENCY VIRUS (HIV) GP41 PEPTIDE DERIVATIVES WITH ENHANCED SOLUBILITY AND ANTIVIRAL ACTIVITY

REFERENCE TO RELATED APPLICATIONS

This application claims priority under 35 U.S.C. § 119(e) to U.S. provisional application Ser. No. 60/412,797, filed Sep. 24, 2002.

BACKGROUND OF THE INVENTION

1. Field of the Invention

This invention relates to human immunodeficiency virus (hereinafter "HIV") gp41 C-terminal peptide derivatives that are inhibitors of viral infection and/or exhibit antifusogenic properties. In particular, this invention relates to peptide derivatives having inhibiting activity against HIV and simian immunodeficiency virus (hereinafter "SIV"), with improved solubility and extended duration of action for the treatment of the respective viral infections.

2. Review of Related Art

Membrane fusion events are commonplace in normal cell biological processes, and membrane fusion is also involved in a variety of disease states, including, for example the entry of enveloped viruses into cells. Some enveloped viruses fuse with target cells by specific binding reactions between proteins of the virus envelop and cell surface proteins which trigger conformational changes in associated viral proteins that in turn promote fusion of the viral envelop with the cell membrane.

One enveloped virus, HIV, is a member of the lentivirus family of retroviruses, and there are two prevalent types of HIV, HIV-1 and HIV-2, with various strains of each having been identified. The fusion of HIV and its host cells is mediated by the binding of viral envelop proteins gp120 and gp41, with the CD4 glycoprotein and a chemokine co-receptor on the cell surface. Binding of gp120 to CD4 on the surface of T cells and to a co-receptor (e.g., CCR5 or CXCR4) is followed by insertion of gp41 into the membrane of the target cell; then helicies from the N-terminal portion of gp41 form coiled coil structures with helicies from the C-terminal portion of the same protein, which draws the virus and the cell together for fusion (Malashkevich, et al., *Proc. Natl. Acad. Sci. U S A,* 1998 Aug. 4;95(16):9134-9).

Peptides are known to inhibit or otherwise disrupt membrane fusion-associated events, including, for example, inhibiting retroviral transmission to uninfected cells. Peptides from the second heptad repeat region of HIV envelop protein gp41, including T20 (DP178) and C34, have shown potent anti-viral activity against HIV in vitro (see Wild, et al., 1994, *Proc. Natl. Acad. Sci. USA,* 91:9770-4; Chan, et al., 1998, *Proc. Natl. Acad. Sci. USA,* 95:15613-15617). The demonstrated anti-viral activity includes inhibiting $CD4^+$ cell infection by free virus and/or inhibiting HIV-induced syncytia formation between infected and uninfected $CD4^+$ cells. The inhibition is believed to occur by binding of these peptides to the first heptad repeat region in gp41, thus preventing the first and second heptad repeat regions from forming the fusogenic hairpin structure.

While many of the anti-viral or anti-fusogenic peptides described in the art exhibit potent anti-viral and/or anti-fusogenic activity in vitro, they suffer from short half-life in vivo, primarily due to rapid serum clearance and peptidase and protease activity. This in turn greatly reduces their effective anti-viral activity. There is therefore a need for a method of prolonging the half-life of peptides in vivo without substantially affecting the anti-fusogenic activity.

One method for prolonging the half-life of peptides is disclosed in U.S. Pat. No. 5,612,034, which describes a method for covalently coupling a therapeutic peptide to a native protein found in the blood stream. The peptide is modified with a chemically reactive moiety that is capable of reacting with fuctionalities present on proteins in the blood stream. Upon injection of the modified peptide into the blood stream, it is linked to a long-lived blood component forming a long-lived depot of the peptide. However, since the molecular weight of proteins in the blood stream ranges between 50-600 kD, there is concern that the biological activity of such linked peptides may be compromised by steric hinderance of the much larger size protein.

An attempt to prolong the half-life of a known anti-fusogenic peptide is disclosed in International Patent Publication WO 00/69902 (hereinafter "the '902 publication") by Conjuchem, Inc. In this disclosure, DP178 is modified by attaching 3-maleimidopropionic acid by an amide link to the epsilon amino group of lysine which is in turn linked by peptide bond to the C-terminal Phe of DP178. The '902 publication also proposes analogs of the modified DP178 which are either truncations of DP178 or corresponding fragments of gp41 from other HIV viral isolates. The '902 publication does not suggest any other design criteria for anti-fusogenic peptides.

Therefore, there remains a need for a method of prolonging the half-life of peptides in vivo without substantially affecting the anti-fusogenic activity.

SUMMARY OF THE INVENTION

The present invention is directed to HIV gp41 peptide derivatives having anti-viral, virostatic and/or anti-fusogenic activity, including but not limited to the modified peptides of Tables 1, 2 and 3 and FIG. 1, as well as modified and derivatized forms thereof (hereinafter collectively referred to as "variant gp41 peptides"). These variant gp41 peptides provide for an increased in vivo stability and a reduced susceptibility to peptidase or protease degradation. As a result, the variant gp41 peptides minimize the need for more frequent, or even continual, administration as would be expected with unmodified HIV gp41 peptides. The present peptide derivatives, and derivatives made using methods of the invention for gp41-like sequences from other viruses, can be used, e.g., as a prophylactic against and/or treatment for infection of a number of viruses, including but not limited to HIV and SIV.

In accordance with the present invention, there are now provided peptide derivatives having enhanced solubility and antiviral activity when compared with the corresponding unmodified peptide sequence of HIV gp41. More specifically, the present invention is concerned with compounds of the formulas illustrated in Tables 1, 2 and 3 and FIG. 1 infra, which include peptide derivatives capable of reacting with thiol groups on a blood component, either in vivo or ex vivo, to form a stable covalent bond.

TABLE 1

| Peptide Fragments of gp41 and Modified Analogs | |
|---|---|
| Ac-SLEQIWNNMT WEEWDREINN YTELIHELIE ESQNQQEKNE QELL-NH2<br>FB005 | (SEQ ID NO:1) |
| Ac-WEEWDREINN YTKLIHELIE ESQNQQEKNE QELL-NH2<br>FB006 | (SEQ ID NO:2) |
| Ac-WEEWDREINN YTKLIHELIE ESQNQQEKNE QELL-NH2<br>FB066 | (SEQ ID NO:7) |
| Ac-WQE WEQKITALLE QAQIQQEKNE YELQKLDKWA SLWEWF-NH2<br>T-1249 | (SEQ ID NO:3) |
| Ac-YTSLIHSLIE ESQNQQEKNE QELLELDKWA SLWNWF-NH2<br>T-20 | (SEQ ID NO:4) |
| Ac-WMEWDREINN YTSLIHSLIE ESQNQQEKNE QELL-NH2<br>C-34 | (SEQ ID NO:5) |

TABLE 2

Maleimide Modified Peptides

Ac- SLEQIWNNMTWEEWDREINNYT- 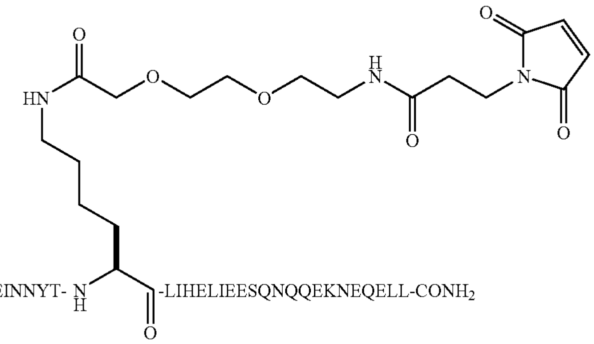 -LIHELIEESQNQQEKNEQELL-CONH$_2$

FB005M (SED ID NO:8)

Ac-SLEQIWNNMTWEEWDREINNYTELIHELIEESQNQQEKNEQELL- 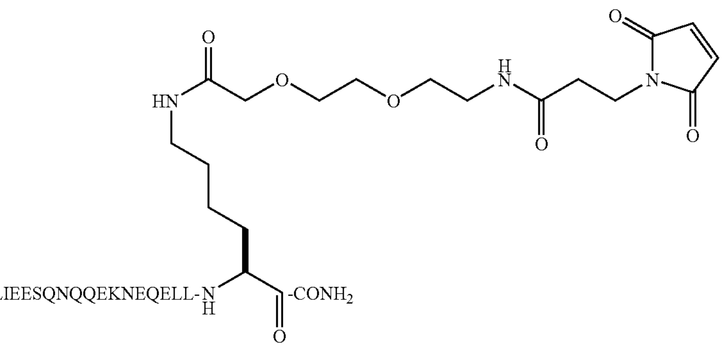 -CONH$_2$

FB005CM (SEQ ID NO:9)

TABLE 2-continued
Maleimide Modified Peptides
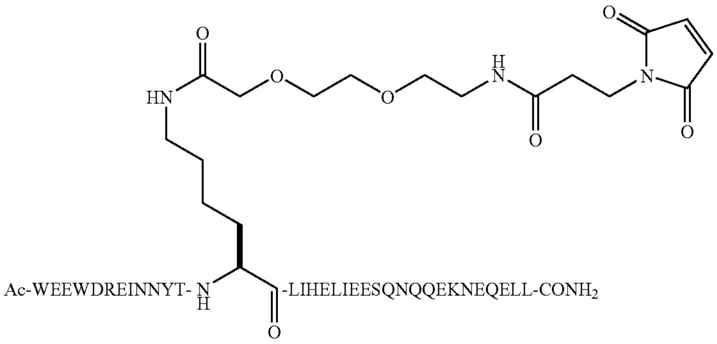
FB006M (SEQ ID NO:10)
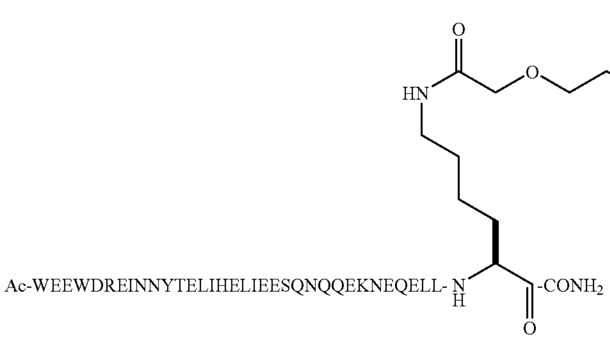
FB007M (SEQ ID NO:11)
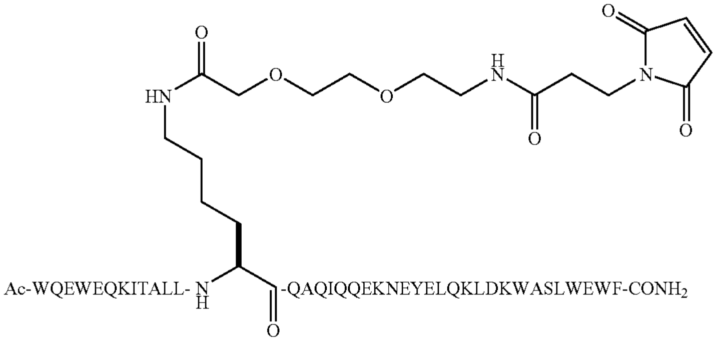
FB010M (SEQ ID NO:12)
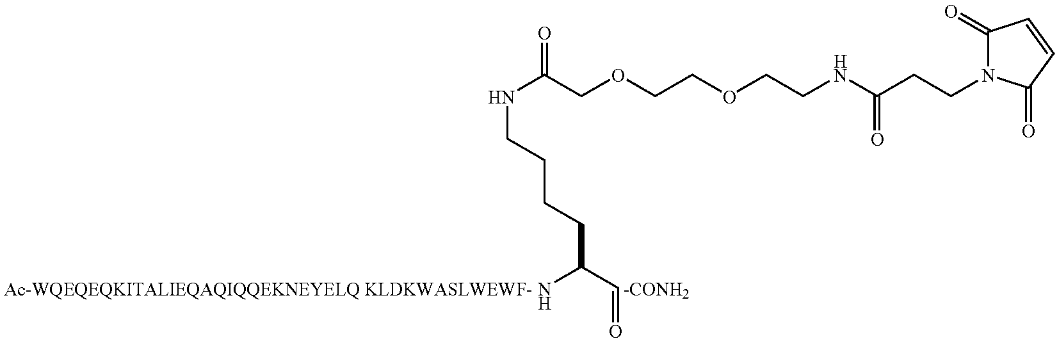
FB010KM (SEQ ID NO:13)

TABLE 2-continued

Maleimide Modified Peptides

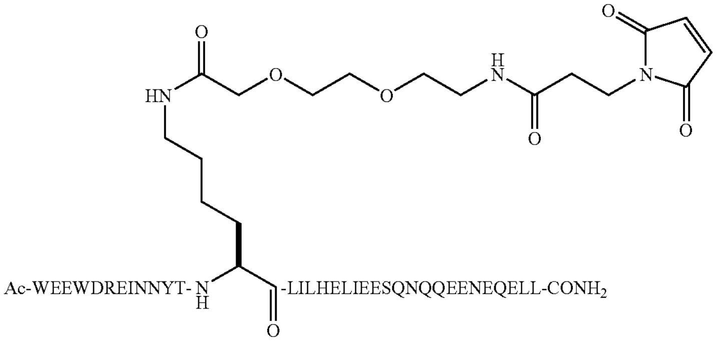

FB066M (SEQ ID NO:14)

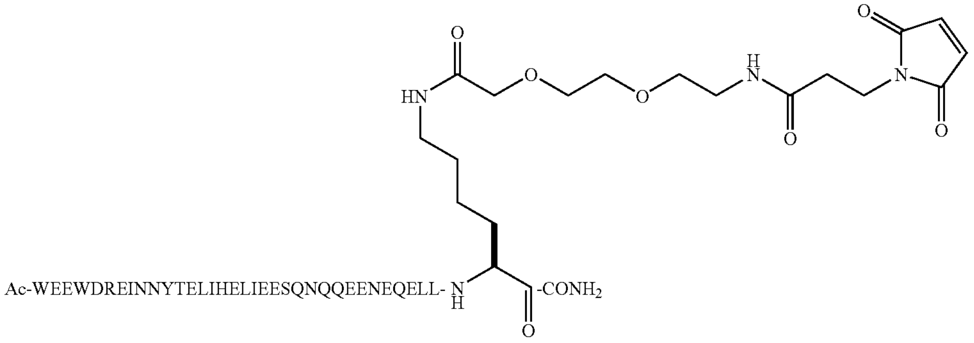

FB066KM (SEQ ID NO:15)

This invention provides novel compositions, containing peptides having modification of predetermined residues (i.e., point mutations) relative to the native peptide which are introduced to improve activity and solubility. The predetermined residues consist of the underlined amino acid residues of the peptide sequences found in Table 3. The peptides having modified residues include, but are not limited to, substituted amino acid residues wherein amino acid residues having either the properties of increased hydrophilic or hydrophobicity are substituted for native amino acid residues. The variant gp41 peptides may also be substituted with amino acid residues having high alpha helical-forming propensities. Alternatively, the peptides having modified residues include, but are not limited to, derivatized amino acid residues wherein a coupling group is conjugated to a pre-determined amino acid residue, thereby allowing covalent bonding of the derivatized peptide to a blood component.

In another aspect, this invention provides pharmaceutical compositions comprising the derivatives of the above formulae in combination with a pharmaceutically acceptable carrier. Such compositions are useful for inhibiting the activity of HIV (including HIV-1, HIV-2 and all serotypes thereof) and SIV.

In a further embodiment of the present invention, there is provided a method for inhibiting the infection of HIV or SIV. The method comprises administering to a subject, preferably a mammal, and most preferably a human, a virus-inhibiting effective amount of one or more variant gp41 peptides, alone or in combination with a pharmaceutical carrier, or in combination with other antiviral agents including other variant gp41 peptides. In a particularly preferred embodiment of the invention, at least one of the variant gp41 peptides, alone or in combination with a pharmaceutical carrier, or in combination with other antiviral agents including other variant gp41 peptides, may be administered to a subject in a virus-inhibiting amount.

In a further aspect of the present invention, there is provided a conjugate comprising at least one of the variant gp41 peptides covalently bonded to a blood component. In one embodiment of the invention, preferred blood components for reaction with the compounds of this invention include proteins such as immunoglobulins, including IgG and IgM, serum albumin, ferritin, steroid binding proteins, transferrin, thyroxin binding protein, α-2-macroglobulin etc., serum albumin and IgG being a more preferred embodiment, and serum albumin being the most preferred embodiment of the invention.

In a further aspect of the present invention, there is provided a method for extending the in vivo half-life of the variant gp41 peptides in a subject, the method comprising covalently bonding one or more of the variant gp41 peptides to a blood component.

In another embodiment of the invention, a method is provided for the design, synthesis and testing of novel peptides having anti-viral, virostatic or anti-fusogenic activity against a variety of viruses. The method involves screening of viral proteins involved with cellular entry to identify peptide sequences therein harboring alpha-helical forming propensities, and designing compositions based off of these peptides that can be used to treat the diseases caused by the same viruses. The method also contemplates in vitro testing of the peptide compositions to verify anti-viral, virostatic or anti-fusogenic activity.

BRIEF DESCRIPTION OF THE FIGURE

FIG. 1—FIG. 1 shows the aligned sequences of various peptides disclosed in the present invention.

DETAILED DESCRIPTION OF THE INVENTION

As used herein, "derivatization" shall mean the addition of coupling groups to peptide sequences. Representative coupling groups are more particularly provided infra.

As used herein, "modification" shall mean the substitution of a first amino acid in a native peptide sequence by a second amino acid. The second amino acid may be selected from the non-limiting group of hydrophilic amino acids, hydrophobic amino acids, amino acids having helical propensities, non-naturally occurring amino acids and the D-isomers of the naturally occurring L-amino acids.

Fusion of HIV-1 and related lentiviruses with target cells can be inhibited by peptide fragments of the native viral envelop proteins which accomplish the fusion. These peptide fragments can bind to the envelop proteins and block binding of distal portions of the viral envelope proteins, thereby inhibiting conformational changes in the native protein that are critical to effect the fusion of HIV-1 to target cells. These peptides, by blocking fusion of the virus with the cells, interrupt the infectious process necessary for disease progression.

The present invention improves on the properties of existing anti-viral and anti-fusogenic peptides and provides novel peptide compositions useful to treat HIV and SIV. The viruses that may be inhibited by the peptides of this invention include, but are not limited to, the human retrovirus HIV (including HIV-1 and HIV-2, as well as all other serotypes thereof) and SIV.

Modified Peptides

Modified, derivatized peptides with anti-fusogenic activity against lentiviruses can be prepared according to this invention. The anti-fusogenic peptides are helix-forming peptides based on native gp41 protein sequence, which are modified by changing selected amino acids of the peptides. The modified amino acids are selected to avoid disrupting the interactions which contribute to the formation of coiled-coil complexes with helicies of viral envelop protein gp41. In one embodiment, the amino acid residues selected for modification are those whose side chains are away from the coiled-coil interface. These residues are substituted with alternative residues that will enhance either the hydrophobic or hydrophilic properties of the peptides, or alternatively are derivatized to provide reactive moieties that enable covalent bonding of the peptides to circulating blood proteins. The introduction of hydrophilic residues into a peptide sequence will increase the solubility of the peptide. The introduction of hydrophobic residues into a peptide sequence will decrease the solubility of the peptide. In one embodiment of the invention, modified peptides include the peptides designated FB005, FB006 and FB066, and especially derivatives of these peptides with maleimide coupling moieties, such as 3-maleimidopropionic acid coupled to lysine through [2-(2-amino-ethoxy) ethoxy] acetic acid, or other equivalent coupling structures. In another embodiment of the invention, amino acids in the peptide sequence are substituted with amino acids having a propensity to form alpha-helices.

Alternatively, chemical groups can be added at their amino and/or carboxy termini, such that for example, the stability, reactivity and/or solubility of the peptides is enhanced. For example, hydrophobic groups such as carbobenzoxyl, dansyl, acetyl or t-butyloxycarbonyl groups, may be added to the peptides' amino termini. Likewise, an acetyl group or a 9-fluorenylmethoxy-carbonyl group may be placed at the peptides' amino termini. Additionally, the hydrophobic group, t-butyloxycarbonyl, or an amido group may be added to the peptides' carboxy termini. Similarly, a para-nitrobenzyl ester group may be placed at the peptides' carboxy termini. Techniques for introducing such modifications are well known to those of skill in the art.

The peptides may be synthesized such that their steric configuration is altered. For example, the D-isomer of one or more of the amino acid residues of the peptide may be used, rather than the usual L-isomer. In one embodiment of the invention, at least two or more amino acid substitutions comprise D-isomers of the naturally occurring L-amino acids. In another embodiment of the invention, each of the naturally occurring L-amino acids in the complete peptide sequence is substituted with a D-isomer of the same amino acid. The invention also contemplates that at least one of the amino acid residues of the variant gp41 peptides may be substituted by one of the well known non-naturally occurring amino acid residues. In another embodiment of the invention, any combination of substitutions of the D-isomers of the naturally occurring L-amino acids, or non-naturally occurring amino acids, may be made to the variant gp41 peptides. Alterations such as these may serve to increase the stability, protease-resistance, activity, reactivity and/or solubility of the variant gp41 peptides.

Non-naturally occurring amino acids are well known in the art. Furthermore, methods of synthesizing peptides having either D-isomers of the naturally occurring L-amino acids or non-naturally occurring amino acids are also well known in the art (See, for example, the disclosures of U.S. Pat. Nos. 5,840,697 and 6,268,479, as well as *Biochemistry* (Chap. 4), D. Voet and J. G. Voet, Wiley & Sons (1990), which are herein incorporated by reference), and are also within the contemplation of this invention.

In one embodiment of the invention, modified peptides include the peptides designated FB005, FB006 and FB066, and especially derivatives of these peptides with maleimide coupling moieties, such as 3-maleimidopropionic acid coupled to lysine through [2-(2-amino-ethoxy) ethoxy]acetic acid, or other equivalent coupling structures.

The invention further encompasses variant gp41 peptides wherein amino acid residues thereof are substituted with either hydrophilic or hydrophobic residues, thereby altering the aqueous traits of the peptides. Alternatively, other amino acid residues of the variant gp41 peptides are derivatized with a maleimide linking moiety. In a preferred embodiment of the invention, the underlined amino acid residues in the following variant gp41 peptides (presented in Table 3) are substituted with hydrophilic or hydrophobic residues, or alternatively are derivatized with a maleimide linking moiety. Any other peptides encompassed by this invention having a C-terminal lysine residue may also have that C-terminal lysine residue substituted with hydrophilic residues, or alternatively derivatized with a maleimide linking moiety:

TABLE 3

| | |
|---|---|
| YTSLIHSLIEESQNQQEKNEQELLELDKWASLWNWF | (SEQ ID NO:4) |
| WQEWEQKITALLEQAQIQQEKNEYELQKLDKWASLWEWF | (SEQ ID NO:3) |
| WMEWDREINNYTSLIHSLIEESQNQQEKNEQELL | (SEQ ID NO:5) |
| WQEWERKVDFLEENITALLEEAQIQQEKNMYELQ | (SEQ ID NO:6) |
| SLEQIWNNMTWEEWDREINNYTELIHELIEESQNQQEKNEQELL | (SEQ ID NO:1) |
| WEEWDREINNYTKLIHELIEESQNQQEKNEQELL | (SEQ ID NO:2) |
| WEEWDREINNYTKLIHELIEESQNQQEENEQELL | (SEQ ID NO:7) |
| SLEQIWNNMTWEEWDREINNYTXLIHELIEESQNQQEKNEQELL | (SEQ ID NO:8) |
| SLEQIWNNMTWEEWDREINNYTELIHELIEESQNQQEKNEQELLX | (SEQ ID NO:9) |
| WEEWDREINNYTXLIHELIEESQNQQEKNEWELL | (SEQ ID NO:10) |
| WEEWDREINNYTELIHELIEESQNQQEKNEQELLX | (SEQ ID NO:11) |
| WQEWEQKITALLXQAQIQQEKNEYELQKLDKWASLWEWF | (SEQ ID NO:12) |
| WQEWEQKITALIEQAQIQQEKNEYELQKLDKWASLWEWFX | (SEQ ID NO:13) |

Hydrophilic amino acids which may be substituted for any of the underlined amino acids include those amino acids listed in Table 4.

Hydrophobic amino acids which may be substituted for any of the underlined amino acids include those amino acids listed in Table 5.

Additionally, any of the underlined amino acid residues presented in Table 3 may be derivatized with a maleimide linking moiety, thereby providing the amino acid residue with which the variant gp41 peptide(s) may be covalently bonded to the available thiol group(s) present on blood components. In a preferred embodiment of the invention, lysine residues are derivatized with a maleimide linking moiety. In a particularly preferred embodiment of the invention, lysine residue(s) derivatized with a maleimide linking moiety is covalently bonded to a thiol group(s) present on a blood component.

In another embodiment of the invention, any of the underlined amino acid residues presented in Table 3 may be substituted with amino acids having high helical propensity (See Creamer, T., et al., Alpha-helix-forming propensities in peptides and proteins. *Proteins*, Jun; 19(2):85-97 (1994)). Amino acids having high helical propensity are listed in Table 6 in descending order of α-helical propensity. Because the active conformation of these peptides is believed to be alpha helical when bound to the viral target gp41, increased tendencies to form helices can potentially increase the antiviral activity.

TABLE 4

Hydrophilic Amino Acids

| Amino Acid | Abbreviation |
|---|---|
| Arginine | Arg |
| Lysine | Lys |
| Aspartic Acid | Asp |
| Glutamic Acid | Glu |
| Asparagine | Asn |
| Glutamine | Gln |
| Histidine | His |
| Serine | Ser |
| Threonine | Thr |
| Glycine | Gly |

TABLE 5

Hydrophobic Amino Acids

| Amino Acid | Abbreviation |
|---|---|
| Alanine | Ala |
| Isoleucine | Ile |
| Leucine | Leu |
| Methionine | Met |
| Phenylalanine | Phe |
| Tryptophan | Trp |
| Valine | Val |
| Tyrosine | Tyr |

TABLE 6

Amino Acids having high helical propensity[1]

| Amino Acid | α-Helical Preference |
|---|---|
| Glutamic acid | 1.59 |
| Alanine | 1.41 |
| Leucine | 1.34 |
| Methionine | 1.30 |
| Glutamine | 1.27 |
| Lysine | 1.23 |
| Arginine | 1.21 |
| Phenylalanine | 1.16 |
| Isoleucine | 1.09 |
| Histidine | 1.05 |
| Tryptophan | 1.02 |
| Aspartic acid | 0.99 |
| Valine | 0.90 |
| Threonine | 0.76 |
| Asparagine | 0.76 |
| Tyrosine | 0.74 |
| Cysteine | 0.66 |
| Serine | 0.57 |
| Glycine | 0.43 |
| Proline | 0.34 |

[1]Source: T. E. Creighton, Proteins:StructureandMolecularProperties (2nd Ed.), W.H. Freeman and Co., 1993.

Generally speaking, peptides of the invention are C-34 analogs comprising five heptads of one alpha helix of a coiled coil protein complex, preferred analogs having maleimide coupling groups and residues more polar than the parent sequence substituted at residue 2 of 7 of the first heptad, residue 6 of 7 of the second heptad, residue 3 of 7 of the third heptad and/or residue 7 of 7 of the fourth heptad. In another embodiment of the invention, peptides of the invention encompass these above-recited peptides, but further include an additional 10 residues from gp41 introduced at the N-terminus of the C-34 peptide.

Peptide FB006 is based on the C34 peptide with the second and the seventeenth residues mutated to glutamate, and the thirteenth residue mutated to lysine. The mutation positions were selected based on the crystal structure of the N36/C34 complex. The selection criterion is that these residues are not involved in binding to the N36 helices. Mutations to glutamate and lysine are aimed to improve the solubility and helical propensity, which is the tendency to form a helix in aqueous solution. Because it is believed that the active conformation of C34 is helical as in the N36/C34 crystal structure, enhanced helical propensity thus should improve the biological activity. Peptides FB005, FB006, FB066, FB005M, FB005CM, FB006M, and FB007M also contain these substitutions.

Variant gp41 peptides encompass the peptide sequences listed in Tables 1, 2 and 3, and FIG. 1, as well as modified and derivatized forms thereof. Peptide FB005 is based on the FB006 peptide, but has an additional 10 amino acid residues located at the N-terminus relative to other variant gp41 peptides.

Peptide FB066 is based on FB006. It is different from FB006 in that it harbors a single amino acid substitution, changing the lysine at position 28 to a glutamic acid. This change leaves the $13^{th}$ amino acid residue as the only lysine residue to function as the conjugation site. This change significantly simplifies the synthesis of analogs with maleimide modifications.

The invention also provides derivatives based on FB005, FB006, and T-1249 (see WO 01/03723) which can conjugate with serum albumin to become long lasting inhibitors. Peptides FB005M and FB005CM are based on the FB005 sequence; peptides FB006M and FB007M are based on FB006 sequence; and peptides FB010M and FB010KM are based on the T-1249 sequence.

The method of selecting the linkage site on the peptide to enable linkage to the blood protein carrier is also novel. The inventors found that linking the variant gp41 peptide to albumin via an internal Lysine residue of the peptide yields a conjugate with improved efficacy over a C-terminal linkage. The $IC_{50}$[2] for FB006, FB006M, and FB007M are 1.4, 3.9 and 9.1 nM respectively. FB006 is the native peptide, FB006M is a modified peptide complex harboring a maleimide linkage at the $13^{th}$ residue, while FB007M is linked at the C-terminus. When FB006M is linked to serum albumin, the amount needed for antiviral effect increases by 2.8-fold while linking to albumin via the C-terminal linkage of FB007M causes the $IC_{50}$ to increase in value by 6.5-fold. Although linking to a carrier molecule was anticipated to extend the ½-life of the peptide, conceptually conjugation to albumin (a 66 kDa protein) was also expected to block the biological activity of the peptides by providing a steric hinderance. Unexpectedly, however, when the inventors prepared FB006M peptides and conjugated it to albumin, it was found that the antiviral activity of the complex was not appreciably compromised (increase only 2.8-fold).

[2] The $IC_{50}$ value is the drug concentration for achieving 50% viral inhibition, and $TC_{50}$ value is the drug concentration for achieving 50% cytotoxicity.

Coupling groups of the invention are chemical groups capable of forming a covalent bond with a functionality present on a blood component. Coupling groups are generally stable in an aqueous environment. The reactive functionalities which are available on blood components for covalent bonding to the coupling groups are primarily amino groups, carboxyl groups and thiol groups. In one embodiment of the invention, coupling groups include, but are not limited to, reactive double bonds, carboxy, phosphoryl, or convenient acyl groups, either as an ester or a mixed anhydride, or an imidate, thereby capable of forming a covalent bond with functionalities such as amino groups, hydroxy groups or thiol groups at the target site on mobile proteins, in particular on blood proteins. Reactive ester coupling groups consist of phenolic compounds, thiol esters, alkyl esters, phosphate esters, or the like. In a particularly preferred embodiment of the invention, coupling groups consist of succinimidyl or maleimido groups.

The focus of the present invention is to modify gp41 peptide sequences to confer improved bio-availability, extended half-life and better distribution (through selective conjugation of the peptide onto a protein carrier) to the peptides without substantially modifying the anti-viral, virostatic or anti-fusogenic properties of the peptides. Derivatization of variant gp41 peptides as described herein allows the derivatized peptides to react with groups on blood components (particularly available thiol groups) to form stable covalent bonds. Preferred derivatives of variant gp41 peptides are designed to specifically react with thiol groups on mobile blood proteins. Such reaction is established by covalent bonding of the peptide having a maleimide link to a thiol group on a mobile blood protein such as serum albumin or IgG. Thus, one embodiment of the invention comprises a modified peptide covalently linked to a blood protein, including a mobile blood protein. A particularly preferred embodiment of the invention involves covalent bonding of the modified peptide to serum albumin.

The blood components to which the present derivatives of variant gp41 peptides covalently bond may be either fixed or mobile. Fixed blood components are non-mobile blood components and include tissues, membrane receptors, interstitial proteins, fibrin proteins, collagens, platelets, endothelial cells, epithelial cells and their associated membrane and membraneous receptors, somatic body cells, skeletal and smooth muscle cells, neuronal components, osteocytes and osteoclasts, and all body tissues especially those associated with the circulatory and lymphatic systems. Mobile blood components are blood components that do not have a fixed situs for any extended period of time, generally not exceeding 5 minutes, and more usually one minute. These blood components are not membrane-associated and are present in the blood for extended periods of time in a minimum concentration of at least 0.1 μg/ml. Mobile blood components include serum albumin, transferrin, ferritin and immunoglobulins such as IgM and IgG. The half-life of mobile blood components is at least about 12 hours. A carrier of choice for this invention is albumin conjugated through its free thiol.

In another embodiment of the invention is provided a method for generating peptide fusion inhibitors having anti-viral, virostatic or anti-fusogenic activity to prevent or treat infection by viruses, including retroviruses. According to the method, viral proteins involved in viral entry into a cell and/or having fusogenic activity are identified. The amino acid sequences of said viral proteins are then screened for alpha helix-forming regions believed to be involved in protein-protein association. One of skill in the art can use computer-based algorithms to screen for alpha helix-forming regions of protein sequences. Computer-based algorithms useful for identifying alpha helix-forming regions include, but are not limited to, Garnier-Robson and Chou-Fasman indices of helical preference, available in such program suites as DNASTAR.

Peptides, derived from the alpha helix-forming regions of the viral proteins, can be designed according to the methods discussed supra by substituting predetermined amino acid residues with amino acid residues that enhance the hydrophilicity, hydrophobicity or alpha helix-forming tendencies of the peptide sequence. Alternatively, substitutions using D-isomers of the naturally occurring L-amino acids or non-naturally occurring amino acids may be made to the peptides of the invention. In one embodiment of the invention, at least two or more amino acid substitutions comprise D-isomers of the naturally occurring L-amino acids. In another embodiment of the invention, the complete peptide sequence comprises D-isomers of the naturally occurring L-amino acids. Alterations such as these may serve to increase the stability, protease-resistance, activity, reactivity and/or solubility of the peptides of the invention.

Derivatized forms of these peptides are useful as treatments having extended half-lives once conjugated to blood components such as, for example, serum albumin. Peptide sequences comprising D-isomers of the naturally occurring L-amino acids are expected to demonstrate increased resistance to protease activity in a manner proportional to the number of D-isomers of the naturally occurring L-amino acids present in the peptide sequence, independent of whether the peptides are conjugated to blood components.

This method of the invention further contemplates in vitro testing of the peptide compositions to verify anti-viral, virostatic or anti-fusogenic activity. For example, one of skill in the art could modify the teachings of Example 9 herein to similarly construct an assay that screens for anti-viral activity. By way of a non-limiting example, one of skill in the art could utilize or modify the teachings of Example 9 to test the effects of anti-viral peptides in the presence of a virus having specificity for a cell type, such as for example, PBMCs, in order to determine the $IC_{50}$ and $TC_{50}$ values. Following infection of a cell type in both the presence and absence of peptide inhibitors (with appropriate controls), and incubation of said cells, viral titers are determined and the $IC_{50}$ and $TC_{50}$ values determined.

Viruses to which this method of the invention is applicable include, but are not limited to, human retroviruses, including HIV-1 and HIV-2, human T-lymphocyte viruses (HTLV-I and HTLV-II), and non-human retroviruses, including bovine leukosis virus, feline sarcoma virus, feline leukemia virus, simian immunodeficiency virus (SIV), simian sarcoma virus, simian leukemia, and sheep progress pneumonia virus. Non-retroviral viruses may also be inhibited by the anti-viral, virostatic or anti-fusogenic peptides, including but not limited to, human respiratory syncytial virus (RSV), canine distemper virus, Newcastle disease virus, human parainfluenza virus (HPV), influenza viruses, measles virus, Epstein-Barr viruses, hepatitis B viruses, and simian Mason-Pfizer viruses. Non-enveloped viruses may also be inhibited by the peptides of the invention, including but not limited to, picomaviruses such as polio viruses, hepatitis A virus, enteroviruses, echoviruses, coxsachie viruses, papovaviruses such as papilloma virus, parvoviruses, adenoviruses, and reoviruses.

Peptide Synthesis

The derivatized variant gp41 peptides may be synthesized by standard methods of solid phase peptide chemistry well known to any one of ordinary skill in the art. For example, the peptides may be synthesized by solid phase chemistry techniques following the procedures described by Steward et al. in Solid Phase Peptide Synthesis, 2nd Ed., Pierce Chemical Company, Rockford, Ill., (1984) using a Rainin PTI Symphony synthesizer. Alternatively, peptides fragments may be synthesized and subsequently combined or linked together to form the gp41 peptide sequences in solution (segment condensation, as described, for example, in U.S. Pat. No. 6,281,331 (the disclosures of both of which are herein incorporated by reference)).

For solid phase peptide synthesis, a summary of the many techniques may be found in Stewart et al. in "Solid Phase Peptide Synthesis", W. H. Freeman Co. (San Francisco), 1963 and Meienhofer, Hormonal Proteins and Peptides, 1973, 2 46. For classical solution synthesis, see for example Schroder et al. in "The Peptides", volume 1, Acacemic Press (New York). In general, such methods comprise the sequential addition of one or more amino acids or suitably protected amino acids to a growing peptide chain on a polymer. Normally, either the amino or carboxyl group of the first amino acid is protected by a suitable protecting group. The protected and/or derivatized amino acid is then either attached to an inert solid support or utilized in solution by adding the next amino acid in the sequence having the complimentary (amino or carboxyl) group suitably protected and under conditions suitable for forming the amide linkage. The protecting group is then removed from this newly added amino acid residue and the next amino acid (suitably protected) is added, and so forth.

After all the desired amino acids have been linked in the proper sequence, any remaining protecting groups (and any solid support) are cleaved sequentially or concurrently to yield the final peptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. Protective groups may be required during the synthesis process of the present peptide derivative. These protective groups are conventional in the field of peptide synthesis, and can be generally described as chemical moieties capable of protecting the peptide derivative from reacting with other functional groups. Various protective groups are available commercially, and examples thereof can be found in U.S. Pat. No. 5,493,007, which is herein incorporated by reference. Typical examples of suitable protective groups include acetyl, fluorenylmethyloxycarbonyl (FMOC), t-butyloxycarbonyl (BOC), benzyloxycarbonyl (CBZ), etc. In addition, Table 7 provides both the three letter and one letter abbreviations of the naturally occurring amino acids.

TABLE 7

Naturally Occurring Amino Acids and Their Abbreviations

| Name | 3-letter abbreviation | 1-letter abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |

TABLE 7-continued

| Naturally Occurring Amino Acids and Their Abbreviations | | |
|---|---|---|
| Name | 3-letter abbreviation | 1-letter abbreviation |
| Serine | Ser | S |
| Threonine | Thr | T |
| Tryptophan | Trp | W |
| Tyrosine | Tyr | Y |
| Valine | Val | V |

A particularly preferred method of preparing the variant gp41 peptides involves solid phase peptide synthesis wherein the amino acid α-N-terminal is protected by an acid or base sensitive group. Such protecting groups should have the properties of being stable to the conditions of peptide linkage formation while being readily removable without destruction of the growing peptide chain or racemization of any of the chiral centers contained therein. Examples of N-protecting groups and carboxy-protecting groups are disclosed in Greene, "Protective Groups In Organic Synthesis," (John Wiley & Sons, New York pp. 152-186 (1981)), which is herein incorporated by reference. Examples of N-protecting groups comprise, without limitation, loweralkanoyl groups such as formyl, acetyl ("Ac"), propionyl, pivaloyl, t-butylacetyl and the like; other acyl groups include 2-chloroacetyl, 2-bromoacetyl, trifluoroacetyl, trichloroacetyl, phthalyl, o-nitrophenoxyacetyl, -chlorobutyryl, benzoyl, 4-chlorobenzoyl, 4-bromobenzoyl, 4-nitrobenzoyl and the like; sulfonyl groups such as benzenesulfonyl, p-toluenesulfonyl, o-nitrophenylsulfonyl, 2,2,5,7,8-pentamethylchroman-6-sulfonyl (pmc), and the like; carbamate forming groups such as t-amyloxycarbonyl, benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-ethoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (boc), diisopropylmethoxycarbonyl, isopropyloxycarbonyl, ethoxycarbonyl, methoxycarbonyl, allyloxycarbonyl (Aloc), 2,2,2,-trichloroethoxycarbonyl, phenoxycarbonyl, 4-nitrophenoxycarbonyl, fluorenyl-9-methoxycarbonyl, isobornyloxycarbonyl, cyclopentyloxycarbonyl, adamantyloxycarbonyl, cyclohexyloxycarbonyl, phenylthiocarbonyl and the like; arylalkyl groups such as benzyl, biphenylisopropyloxycarbonyl, triphenylmethyl, benzyloxymethyl, 9-fluorenylmethyloxycarbonyl (Fmoc) and the like and silyl groups such as trimethylsilyl and the like. Preferred α-N-protecting group are o-nitrophenylsulfenyl; 9-fluorenylmethyloxycarbonyl; t-butyloxycarbonyl (boc), isobornyloxycarbonyl; 3,5-dimethoxybenzyloxycarbonyl; t-amyloxycarbonyl; 2-cyano-t-butyloxycarbonyl, and the like, 9-fluorenylmethyloxycarbonyl (Fmoc) being more preferred, while preferred side chain N-protecting groups comprise 2,2,5,7,8-pentamethylchroman-6-sulfonyl (pmc), nitro, p-toluenesulfonyl, 4-methoxybenzene-sulfonyl, Cbz, Boc, and adamantyloxycarbonyl for side chain amino groups like lysine and arginine; Aloc for lysine; benzyl, o-bromobenzyloxycarbonyl, 2,6-dichlorobenzyl, isopropyl, t-butyl (t-Bu), cyclohexyl, cyclopenyl and acetyl (Ac) for tyrosine; t-butyl, benzyl and tetrahydropyranyl for serine; trityl, benzyl, Cbz, p-toluenesulfonyl and 2,4-dinitrophenyl for histidine; formyl for tryptophan; benzyl and t-butyl for aspartic acid and glutamic acid; and triphenylmethyl (trityl) for cysteine.

A carboxy-protecting group conventionally refers to a carboxylic acid protecting ester or amide group. Such carboxy protecting groups are well known to those skilled in the art, having been extensively used in the protection of carboxyl groups in the penicillin and cephalosporin fields as described in U.S. Pat. Nos. 3,840,556 and 3,719,667, the disclosures of which are herein incorporated by reference.

Representative carboxy protecting groups comprise, without limitation, C1-C8 loweralkyl; arylalkyl such as phenethyl or benzyl and substituted derivatives thereof such as alkoxybenzyl or nitrobenzyl groups; arylalkenyl such as phenylethenyl; aryl and substituted derivatives thereof such as 5-indanyl; dialkylaminoalkyl such as dimethylaminoethyl; alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl; cycloalkanoyloxyalkyl groups such as cyclopropylcarbonyloxymethyl, cyclobutylcarbonyloxymethyl, cyclopentylcarbonyloxymethyl, cyclohexylcarbonyloxy-methyl; aroyloxyalkyl such as benzoyloxymethyl, benzoyloxyethyl; arylalkylcarbonyloxyalkyl such as benzylcarbonyloxymethyl, 2-benzylcarbonyloxyethyl; alkoxycarbonylalkyl or cycloalkyloxycarbonylalkyl such as methoxycarbonylmethyl, cyclohexyloxycarbonylmethyl, 1-methoxycarbonyl-1-ethyl; alkoxycarbonyloxyalkyl or cycloalkyloxycarbonyloxyalkyl such as methoxycarbonyloxymethyl, t-butyloxycarbonyl-oxymethyl, 1-ethoxycarbonyloxy-1-ethyl, 1-cyclohexyloxycarbonyloxy-1-ethyl; aryloxy-carbonyloxyalkyl such as 2-(phenoxycarbonyloxy)ethyl, 2-(5-indanyloxycarbonyloxy)-ethyl; alkoxyalkylcarbonyloxyalkyl such as 2-(1-methoxy-2-methylpropan-2-oyloxy)-ethyl; arylalkyloxycarbonyloxyalkyl such as 2-(benzyloxycarbonyloxy)ethyl; arylalkenyloxycarbonyloxyalkyl such as 2-(3-phenylpropen-2-yloxycarbonyloxy)ethyl; alkoxycarbonylaminoalkyl such as t-butyloxycarbonylaminomethyl; alkylaminocarbonyl-aminoalkyl such as methylaminocarbonylaminomethyl; alkanoylaminoalkyl such as acetylaminomethyl; heterocycliccarbonyloxyalkyl such as 4-methylpiperazinylcarbonyloxymethyl; dialkylaminocarbonylalkyl such as dimethylaminocarbonylmethyl, diethylaminocarbonylmethyl; (5-(loweralkyl)-2-oxo-1,3-dioxolen-4-yl)alkyl such as (5-t-butyl-2-oxo-1,3-dioxolen-4-yl)methyl; and (5-phenyl-2-oxo-1,3-dioxolen-4-yl)alkyl such as (5-phenyl-2-oxo-1,3-dioxolen-4-yl)methyl. Representative amide carboxy protecting groups comprise, without limitation, aminocarbonyl and loweralkylaminocarbonyl groups. Of the above carboxy-protecting groups, loweralkyl, cycloalkyl or arylalkyl ester, for example, methyl ester, ethyl ester, propyl ester, isopropyl ester, butyl ester, sec-butyl ester, isobutyl ester, amyl ester, isoamyl ester, octyl ester, cyclohexyl ester, phenylethyl ester and the like or an alkanoyloxyalkyl, cycloalkanoyloxyalkyl, aroyloxyalkyl or an arylalkylcarbonyloxyalkyl ester are preferred. Preferred amide carboxy protecting groups are loweralkylaminocarbonyl groups.

In the solid phase peptide synthesis method, the α-C-terminal amino acid is attached to a suitable solid support or resin. Suitable solid supports useful for the above synthesis are those materials that are inert to the reagents and reaction conditions of the stepwise condensation-deprotection reactions, as well as being insoluble in the media used. The preferred solid support for synthesis of α-C-terminal carboxy peptides is 4-hydroxymethylphenoxyacetyl-4'-methylbenzyhydrylamine resin (HMP resin). The preferred solid support for α-C-terminal amide peptides is an Fmoc-protected Ramage resin, manufactured and sold by Bachem Inc., California.

In preferred syntheses, the linking lysine is protected by Aloc. After the synthesis is complete, the Aloc is cleaved by Pd(Ph3)4 while the peptide is still on the resin, and allows the coupling of the linker molecule and the maleimide group. Specifically, the linker is[2-(2-amino)ethoxyl]ethoxy acetic acid, and the maleimide group is 3'-maleimidopropionic acid. After the modification, the Fmoc groups are removed and the peptide is cleaved off the resin.

At the end of the solid phase synthesis, the peptide is removed from the resin and deprotected, either in successive operations or in a single operation. Removal of the peptide and deprotection can be accomplished conventionally in a single operation by treating the resin-bound polypeptide with a cleavage reagent comprising thioanisole, triisopropyl silane, phenol, and trifluoroacetic acid. In cases wherein the α-C-terminus of the peptide is an alkylamide, the resin is cleaved by aminolysis with an alkylamine. Alternatively, the peptide may be removed by transesterification, e.g. with methanol, followed by aminolysis or by direct transamidation. The protected peptide may be purified at this point or taken to the next step directly. The removal of the side chain protecting groups is accomplished using the cleavage mixture described above. The fully deprotected peptide can be purified by a sequence of chromatographic steps employing any or all of the following types: ion exchange on a weakly basic resin (acetate form); hydrophobic adsorption chromatography on underivatized polystyrene-divinylbenzene (such as Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or phenyl/hexylsilyl-silica bonded phase column packing. The skilled artisan can determine the preferred chromatographic steps or sequences required to obtain acceptable purification of the variant gp41 peptides.

Alternatively, peptide fragments, including addition of the maleimide group can be synthesized in solid phase, and the final derivatized peptide can be obtained by solution coupling of these fragments.

Molecular weights of these peptides may be determined using Electrospray mass spectroscopy or MALDI-TOF mass spectroscopy.

Therapeutic Use of the Modified Peptides

The variant gp41 peptides, including compounds listed in Tables 1, 2 and 3 and FIG. 1, inhibit viral infection of cells, for example, by inhibiting cell-cell fusion or free virus infection. The route of infection may involve membrane fusion, as occurs in the case of enveloped or encapsulated viruses, or some other fusion event involving viral and cellular structures such as cellular receptors.

The variant gp41 peptides may be administered in vivo such that conjugation with blood components occurs in vivo, or they may be first conjugated to blood components ex vivo and the resulting conjugated derivative administered in vivo. In another embodiment of the invention, plasmaphoresis is utilized to separate desired blood components in a patient's blood sample, which are then conjugated to the peptides of the invention prior to administration back to the patient.

Thiol groups are less abundant in vivo than, for example, amino groups in plasma proteins. Hence the maleimide-modified variant gp41 peptide(s) will covalently bond to fewer proteins. For example, in albumin (the most abundant blood protein) there is only one thiol group. Thus, a modified gp41 peptide-maleimide-albumin conjugate will tend to comprise approximately a 1:1 molar ratio of gp41 peptide to albumin. In addition to albumin, IgG molecules (class II) also have free thiols. Since IgG molecules and serum albumin make up the majority of the soluble protein in blood they also make up the majority of the free thiol groups in blood that are available to covalently bond to the variant gp41 peptides.

Further, even among free thiol-containing blood proteins, including IgGs, specific labeling with a maleimide leads to the preferential formation of a modified gp41 peptide-maleimide-albumin conjugate due to the unique characteristics of albumin itself. The single free thiol group of albumin, highly conserved among species, is located at amino acid residue 34 (Cys34). It has been demonstrated recently that the Cys34 of albumin has increased reactivity relative to free thiols on other free thiol-containing proteins. This is due in part to the very low pK value of 5.5 for the Cys34 of albumin. This is much lower than typical pK values for cysteine residues in general, which are typically about 8. Due to this low pK, under normal physiological conditions Cys34 of albumin is predominantly in the ionized form, which dramatically increases its reactivity. In addition to the low pK value of Cys34, another factor which enhances the reactivity of Cys34 is its location, which is in a hydrophobic pocket close to the surface of one loop of region V of albumin. This location makes Cys34 readily available to ligands of all kinds, and is an important factor in Cys34's biological role as free radical trap and free thiol scavenger. These properties make Cys34 highly reactive with gp41 peptides harboring maleimide linkages, and the reaction rate acceleration can be as much as 1000-fold relative to rates of reaction of variant gp41 peptides with maleimide linkages with other free-thiol containing proteins.

Another advantage of modified gp41 peptide-maleimide-albumin conjugates is the reproducibility associated with the 1:1 loading of peptide to albumin specifically at Cys34. Other techniques, such as glutaraldehyde, DCC, EDC and other chemical activations of, e.g, free amines, lack this selectivity. For example, albumin contains 52 lysine residues, 25-30 of which are located on the surface of albumin and therefore accessible for conjugation. Activating these lysine residues, or alternatively modifying variant gp41 peptides to couple through these lysine residues, results in a heterogenous population of conjugates. Even if 1:1 molar ratios of gp41 maleimide peptides to albumin are employed, the yield of amine derivatized albumin will consist of multiple conjugation products, some containing 0, 1, 2 or more gp41 peptides per albumin, and each having the peptide randomly coupled at any one or more of the 25-30 available lysine sites. Given the numerous possible combinations, characterization of the exact composition and nature of each conjugate batch becomes difficult, and batch-to-batch reproducibility is all but impossible, making such conjugates less desirable as a therapeutic.

Additionally, while it would seem that conjugation through lysine residues of albumin would at least have the advantage of delivering more therapeutic agent per albumin molecule, studies have shown that a 1:1 ratio of therapeutic agent to albumin is preferred. In an article by Stehle, et al., "The Loading Rate Determines Tumor Targeting properties of Methotrexate-Albumin Conjugates in Rats," *Anti-Cancer Drugs*, Vol. 8, pp. 677-685 (1988), (incorporated herein by reference in its entirety), the authors report that a 1:1 ratio of the anti-cancer drug methotrexate to albumin conjugated via glutaraldehyde gave the most promising results. These conjugates were preferentially taken up by tumor cells, whereas conjugates bearing 5:1 to 20:1 methotrexate molecules had altered HPLC profiles and were quickly taken up by the liver in vivo. It is postulated that at these higher ratios, conformational changes to albumin diminish its effectiveness as a therapeutic carrier.

Through controlled administration of the variant gp41 peptides in vivo, one can control the specific labeling of albumin and IgG in vivo. In typical administrations, 80-90% of the administered derivatized variant gp41 peptides will label albumin and less than 5% will label IgG. Trace labeling of free thiols such as glutathione will also occur. Such specific labeling is preferred for in vivo use as it permits an accurate calculation of the estimated half-life of the variant gp41 peptides.

In addition to providing controlled specific in vivo labeling, the derivatized variant gp41 peptides can provide specific labeling of serum albumin and IgG ex vivo. Such ex vivo labeling involves the addition of the variant gp41 peptides harboring maleimide linkages to blood, serum or saline solution containing serum albumin and/or IgG. Once conjugation has occurred ex vivo with the variant gp41 peptides, the blood, serum or saline solution can be readministered to the patient's blood for in vivo treatment, or lyophilized.

Variant gp41 peptides may be used alone or in combination to optimize their therapeutic effects. In another embodiment of the invention, variant gp41 peptides are co-administered with one or more additional antiviral HIV treatments. Additional antiviral HIV treatments that can be co-administered with the variant gp411 peptides include, but are not limited to, AGENERASE (amprenavir; GlaxoSmithKline); COMBIVIR (lamivudine, zidovudine; GlaxoSmithKline); CRIXIVAN (indinavir, IDV, MK-639; Merck); EMTRIVA (FTC, emtricitabine; Gilead Sciences); EPIVIR (lamivudine, 3TC; GlaxoSmithKline); FORTOVASE (saquinavir; Hoffmann-La Roche); HIVID (Zalcitabine, ddC, dideoxycytidine; Hoffmann-La Roche); INVIRASE (saquinavir mesylate, SQV; Hoffmann-La Roche); KALETRA (lopinavir, ritonavir; Abbott Laboratories); NORVIR (ritonavir, ABT-538; Abbott Laboratories); RESCRIPTOR (Delaviridine, DLV; Pfizer); RETROVIR (zidovudine, AZT, azidothymidine, ZDV; GlaxoSmithKline); REYATAZ (atazanavir sulfate; Bristol Myers-Squibb); SUSTIVA (efavirenz; Bristol Myers-Squibb); TRIZIVIR (abacavir, zidovudine, lamivudine; GlaxoSmithKline); VIDEX EC (enteric coated didanosine; Bristol Myers-Squibb); VIDEX (didanosine, ddI, dideoxyinosine; Bristol Myers-Squibb); VIRACEPT (nelfinavir mesylate, NFV; Agouron Pharmaceuticals); VIRAMUNE (nevirapine, BI-RG-587; Boehringer Ingelheim); VIREAD (tenofovir disoproxil fumarate; Gilead); ZERIT (stavudine, d4T; Bristol Myers-Squibb); ZIAGEN (abacavir; GlaxoSmithKline).

In an additional embodiment of the invention, variant gp41 peptides are co-administered with one or more additional compounds used to treat HIV or HIV-induced diseases. These additional compounds that can be co-administered with the variant gp41 peptides include, but are not limited to, TRIMETREXATE GLUCURONATE (for the treatment of *Pneumocystis carinii* pneumonia); GANCICLOVIR (for the treatment of cytomegalovirus retinitis); aerosolized PENTAMIDINE (for the treatment of *Pneumocystis carinii* pneumonia); ERYTHROPOIETIN (for the treatment of Zidovudine-related anemia); ATOVAQUONE (for the treatment of *Pneumocystis carinii* pneumonia); RIFABUTIN (for the treatment of *Mycobacterium avium*); VISTIDE (for the treatment of relapsing cytomegalovirus retinitis); and SEROSTIM (for the treatment of AIDS-related wasting).

Variant gp41 peptides, including but not limited to those peptides provided in Tables 1, 2 and 3, as well as FIG. 1, can be co-administered with one or more additional variant gp41 peptides listed in Tables 1, 2 and 3, as well as FIG. 1. In another embodiment of the invention, variant gp41 peptides, including but not limited to those peptides provided in Tables 1, 2 and 3, as well as FIG. 1, can be co-administered with T-20 or T-1249 peptides.

Variant gp41 peptides are administered in a physiologically acceptable medium, e.g. deionized water, phosphate buffered saline (PBS), saline, aqueous ethanol or other alcohol, plasma, proteinaceous solutions, mannitol, aqueous glucose, alcohol, vegetable oil, or the like. Preferably the pharmaceutical composition comprising the variant gp41 peptides is administered with a pharmaceutically acceptable carrier. Other components which may be added include buffers, where the media are generally buffered at a pH in the range of about 5 to 10, where the buffer will generally range in concentration from about 50 to 250 mM; salt, where the concentration of salt will generally range from about 5 to 500 mM; physiologically acceptable stabilizers, and the like. The compositions may be lyophilized for convenient storage and transport.

Variant gp41 peptides may be administered orally, parenterally, such as intravascularly (IV), intraarterially (IA), intramuscularly (IM), subcutaneously (SC), or the like. Administration may in appropriate situations be by transfusion. In some instances, where reaction of the functional group is relatively slow, administration may be oral, nasal, rectal, transdermal or by aerosol means, where the nature of the conjugate allows for transfer to the vascular system. Usually a single injection will be employed although more than one injection may be used, if desired. The peptide derivative may be administered by any convenient means, including syringe, trocar, catheter, or the like. The particular manner of administration will vary depending upon the amount to be administered, whether a single bolus or continuous administration, or the like. Preferably, the administration will be intravascularly, where the site of introduction is not critical to this invention, preferably at a site where there is rapid blood flow, e.g., intravenously, peripheral or central vein. Other routes may find use where the administration is coupled with slow release techniques or a protective matrix. The intent is that the variant gp41 peptides be effectively distributed in the blood, so as to be able to react with the blood components. The amount of the conjugate administered will vary widely, generally ranging from about 1 mg to 500 mg. The total administered intravascularly will generally be in the range of about 0.5 μg/kg body weight to about 50 mg/kg, more usually about 0.5 mg/kg to about 10 mg/kg.

By bonding to long-lived components of the blood, such as immunoglobulin, serum albumin, red blood cells and platelets, a number of advantages ensue. The activity of the variant gp41 peptides is extended for days to weeks. Only one administration needs to be given during this period of time. Greater specificity can be achieved, since the active compound will be primarily bound to large molecules where it is less likely to be taken up intracellularly and interfere with other physiological processes.

The formation of the covalent bond with the blood component may occur in vivo or ex vivo. For ex vivo covalent bond formation, derivatized variant gp41 peptides are added to blood serum or a saline solution containing purified blood components such as human serum albumin or IgG, to permit covalent bond formation between the derivative and the blood component. In a preferred embodiment, the variant gp41 peptides are reacted with human serum albumin in saline solution. After formation of the conjugate, the latter may be administered to the subject or lyophilized.

The blood of the mammalian host may be monitored for the activity and/or the presence of the variant gp41 peptides. By taking a blood sample from the host at different times, one may determine whether variant gp41 peptides have become bonded to the long-lived blood components in sufficient amount to be therapeutically active and, thereafter, the level of the variant gp41 peptides in the blood. If desired, one may also determine to which of the blood components variant gp41 peptides are covalently bonded. Monitoring may also take place by using assays specific for gp41 peptide activity, HPLC-MS or antibodies directed against variant gp41 peptides.

The variant gp41 peptides can be administered to patients according to the methods described herein and other methods known in the art. Patients for whom therapy is contemplated include patients infected with any of the viruses referred to herein, particularly HIV-1 and HIV-2. Effective therapeutic dosages of the variant gp41 peptides may be determined through procedures well known by those in the art and will take into consideration any concerns regarding potential toxicity of these gp41 peptides.

The variant gp41 peptides can also be administered prophylactically to previously uninfected individuals. This administration can be advantageous in cases where an individual has been subjected to a high risk of exposure to a virus, as can occur when a patient has been in contact with an infected individual and there is a high risk of viral transmission. This can be expecially advantageous where there is no known cure for the virus, such as the HIV virus. By way of a non-limiting example, prophylactic administration of a gp41 peptide would be advantageous in a situation where a health care worker has been exposed to blood from an HIV-infected individual, or in other situations where patients have engaged in high-risk activities that potentially expose those individuals to the HIV virus. Other applications of the variant gp41 peptides encompass administration of the same to individuals harboring a virus, such as HIV, in order to prevent the transmission of the virus from the infected individual to a non-infected individual. Such applications also include the prevention of mother to infant transmission by breast feeding or other daily contacts, or transmission occurring through sexual activity.

In another embodiment of the invention, variant gp41 peptides, including but not limited to those peptides provided in Tables 1, 2 and 3, as well as FIG. 1, can be co-administered with one or more additional peptides listed in Tables 1, 2 and 3, FIG. 1, T-20, T-1249, or other HIV treatments to prevent the replication of HIV (including HIV-1, HIV-2, or all other serotypes thereof) and SIV viral particles in the patient.

Topical Application

The variant gp41 peptides, including those provided in Tables 1, 2 and 3 and FIG. 1 can be used alone or in the form of a composition containing or consisting essentially of an effective concentration of the peptide and a pharmaceutically acceptable carrier. An effective concentration can be determined by observing whether virus infection can be impeded upon application of the agent(s).

The compositions of the invention include topical microbicidal, virostatic or anti-fusogenic uses for both in vitro and in vivo purposes, especially for intravaginal and intrarectal use. For these purposes the modified peptide can be formulated in any appropriate vehicle, provided, that is, that the anti-fusion activity of the modified peptide is not diminished by the vehicle. Thus, the compositions can be in the form of creams, gels, foams, lotions, ointments, tablets, solutions or sprays. The carrier or vehicle diluent can be aqueous or non-aqueous, for example alcoholic or oleaginous, or a mixture thereof, and may additionally contain other surfactants, emollients, lubricants, stabilizers, dyes, perfumes, antimicrobial agents either as active ingredients or as preservatives, and acids or bases for adjustment of pH. The preferred pH is about 4 to 5. Conventional methods are used in preparing the compositions.

Preferably, the pharmaceutically acceptable carrier or vehicle for topically applied compositions is in the form of a liquid, jelly, or foam containing the compound of this invention. The compound can be incorporated into: (a) ointments and jellies, (b) inserts (suppositories, sponges, and the like), (c) foams, (d) douches and (e) cleansing fluids or body washes. The composition is preferably introduced into the vagina of a female or the rectum of a male or female, at about the time of, and preferably prior to, sexual intercourse, but may also be administered to other mucous membranes. The compositions can be employed for the treatment of and for protection against, sexually transmitted diseases including HIV. The manner of administration will preferably be designed to obtain direct contact of the peptide-containing compositions of the invention with the causative agents of sexually transmitted diseases.

For topical applications, the pharmaceutically acceptable carrier may additionally comprise organic solvents, emulsifiers, gelling agents, moisturizers, stabilizers, other surfactants, wetting agents, preservatives, time release agents, and minor amounts of humectants, sequestering agents, dyes, perfumes, and other components commonly employed in pharmaceutical compositions for topical administration.

With regard to the articles provided by the present invention, the compositions of the invention may be impregnated into absorptive substrate materials, such as sponges, or coated onto the surface of solid substrate materials, such as condoms, diaphragms or medical gloves, to deliver the compositions to vaginal or other potentially infectable epithelium, preferably before or during sexual intercourse. Other articles and delivery systems of this type will be readily apparent to those skilled in the art. The presently preferred articles are condoms, which are coated by spraying modified peptides onto the surfaces of the condoms, or by impregnating the peptides into the condom during manufacture by processes known in the art. Preferred coating compositions include silicon which provides lubricity and releases the modified peptide in a time release manner. Bioadhesive polymers may also be used to prolong the time release aspects of the particular topical or other medicament employed.

Solid dosage forms for topical administration include suppositories, powders, tablets, and granules. In solid dosage forms, the compositions may be admixed with at least one inert diluent such as sucrose, lactose, or starch, and may additionally comprise lubricating agents, buffering agents and other components well known to those skilled in the art.

Actual dosage levels of the modified peptides in the compositions and articles of the invention may be varied so as to obtain amounts at the site of sexually transmitted fluids to obtain the desired therapeutic or prophylactic response for a particular peptide and method of administration. Accordingly, the selected dosage level will depend on the nature and site of infection, the desired therapeutic response, the route of administration, the desired duration of treatment and other factors. Generally, the preferred dosage for modified peptides of this invention will be in the range of about 0.01 to 2.0 wt. percent. A preferred topical vaginal dosage form is a cream or suppository as described above containing from 0.01 to 2.0 wt. percent of the composition according to the invention. In each treatment, typically twice daily, from about 1 to about 5 ml of such dosage form is applied intravaginally, preferably high in the vaginal orifice or into the rectum. Greater amounts are generally avoided to minimize leakage.

The methods and compositions of the invention can be used to prevent and treat a broad spectrum of infections by pathogenic microbes.

EXAMPLES

In order to facilitate a more complete understanding of the invention, a number of Examples are provided below. However, the scope of the invention is not limited to specific embodiments disclosed in these Examples, which are for purposes of illustration only.

General

Unless stated otherwise, the synthesis of each variant gp41 peptide was performed using an automated solid-phase procedure on a Symphony Peptide Synthesizer with manual intervention during the generation of the derivative. The synthesis was performed on Fmoc-protected Ramage amide linker resin, using Fmoc-protected amino acids. Coupling was achieved by using O-benzotriazol-1-yl-N,N,N',N'-tetramethyl-uronium hexafluorophosphate (HBTU) as activator in N,N-dimethylformamide (DMF) solution and diisopropylethylamine (DIEA) as base. The Fmoc protective group was removed using 20% piperidine/DMF. All amino acids used during the synthesis possess the L-stereochemistry. Glass reaction vessels were used during the synthesis.

Example 1

Synthesis of FB005

Step 1: The example describes the solid phase peptide synthesis of the compound on a 1 mmole scale. The following protected amino acids were sequentially added to resin: Fmoc-Leu-OH, Fmoc-Leu-OH, Fmoc-Glu(tBu)-OH, Fmoc-Gln(Trt)-OH, Fmoc-Glu(tBu)-OH, Fmoc-Asn(Trt)-OH, Fmoc-Lys(Boc)-OH, Fmoc-Glu(tBu)-OH, Fmoc-Gln(Trt)-OH, Fmoc-Gln(Trt)-OH, Fmoc-Asn(Trt)-OH, Fmoc-Gln (Trt)-OH, Fmoc-Ser(tBu)-OH, Fmoc-Glu(tBu)-OH, Fmoc-Glu(tBu)-OH, Fmoc-Ile-OH, Fmoc-Leu-OH, Fmoc-Glu (tBu)-OH, Fmoc-His-OH, Fmoc-Ile-OH, Fmoc-Leu-OH, Fmoc-Glu-OH, Fmoc-Thr(tBu)-OH, Fmoc-Tyr(tBu)-OH, Fmoc-Asn(Trt)-OH, Fmoc-Asn(Trt)-OH, Fmoc-Ile-OH, Fmoc-Glu(tBu)-OH, Fmoc-Arg(Pbf)-OH, Fmoc-Asp(tBu)-OH, Fmoc-Trp(Boc)-OH, Fmoc-Glu(tBu)-OH, Fmoc-Glu-OH, Fmoc-Trp(Boc)-OH, Fmoc-Thr-OH, Fmoc-Met-OH, Fmoc-Asn-OH, Fmoc-Asn-OH, Fmoc-Trp-OH, Fmoc-Ile-OH, Fmoc-Gln-OH, Fmoc-Glu-OH, Fmoc-Leu-OH, Fmoc-Ser-OH. They were dissolved in N,N-dimethylformamide (DMF) and, according to the sequence, activated using O-benzotriazol-1-yl-N,N, N',N'-tetramethyl-uronium hexafluorophosphate (HBTU) and diisopropylethylamine (DIEA). Removal of the Fmoc protecting group was achieved using a solution of 20% (V/V) piperidine in N,N-dimethylformamide (DMF) for 20 minutes (step 1). The amino group of the final amino acid was acetylated using acetic acid activated using O-benzotriazol-1-yl-N,N,N',N'-tetramethyl-uronium hexafluorophosphate (HBTU) and diisopropylethylamine (DIEA).

Step 2: The peptide was cleaved from the resin using 85% TFA/5% triisopropylsilane (TIPS)/5% thioanisole and 5% phenol, followed by precipitation by dry-ice cold Et2O (Step 2).

Example 2

Synthesis of FB005M

Step 1: The example describes the solid phase peptide synthesis of the compound on a 1 mmole scale. The following protected amino acids were sequentially added to resin: Fmoc-Leu-OH, Fmoc-Leu-OH, Fmoc-Glu(tBu)-OH, Fmoc-Gln(Trt)-OH, Fmoc-Glu(tBu)-OH, Fmoc-Asn(Trt)-OH, Fmoc-Lys(Boc)-OH, Fmoc-Glu(tBu)-OH, Fmoc-Gln(Trt)-OH, Fmoc-Gln(Trt)-OH, Fmoc-Asn(Trt)-OH, Fmoc-Gln (Trt)-OH, Fmoc-Ser(tBu)-OH, Fmoc-Glu(tBu)-OH, Fmoc-Glu(tBu)-OH, Fmoc-Ile-OH, Fmoc-Leu-OH, Fmoc-Glu (tBu)-OH, Fmoc-His-OH, Fmoc-Ile-OH, Fmoc-Leu-OH, Fmoc-Lys(Aloc)-OH, Fmoc-Thr(tBu)-OH, Fmoc-Tyr(tBu)-OH, Fmoc-Asn(Trt)-OH, Fmoc-Asn(Trt)-OH, Fmoc-Ile-OH, Fmoc-Glu(tBu)-OH, Fmoc-Arg(Pbf)-OH, Fmoc-Asp (tBu)-OH, Fmoc-Trp(Boc)-OH, Fmoc-Glu(tBu)-OH, Fmoc-Glu-OH, Fmoc-Trp(Boc)-OH, Fmoc-Thr-OH, Fmoc-Met-OH, Fmoc-Asn-OH, Fmoc-Asn-OH, Fmoc-Trp-OH, Fmoc-Ile-OH, Fmoc-Gln-OH, Fmoc-Glu-OH, Fmoc-Leu-OH, Fmoc-Ser-OH. They were dissolved in N,N-dimethylformamide (DMF) and, according to the sequence, activated using O-benzotriazol-1-yl-N,N, N',N'-tetramethyl-uronium hexafluorophosphate (HBTU) and diisopropylethylamine (DIEA). Removal of the Fmoc protecting group was achieved using a solution of 20% (V/V) piperidine in N,N-dimethylformamide (DMF) for 20 minutes (step 1). The amino group of the final amino acid was acetylated using acetic acid activated using O-benzotriazol-1-yl-N,N,N',N'-tetramethyl-uronium hexafluorophosphate (HBTU) and diisopropylethylamine (DIEA).

Step 2: The selective deprotection of the Lys (Aloc) group was performed manually and accomplished by treating the resin with a solution of 3 eq of Pd(PPh3)4 dissolved in 5 mL of C6H6CHCl3 (1:1): 2.5% NMM (v:v): 5% AcOH (v:v) for 2 h (Step 2). The resin is then washed with CHCl3 (6×5 mL), 20% AcOH in DCM (6×5 mL), DCM (6×5 mL), and DMF (6×5 mL).

Step 3: The synthesis was then re-automated for the addition of the Fmoc-AEEA-OH and the 3-maleimidopropionic acid (Step 3). Between every coupling, the resin was washed 3 times with N,N-dimethylformamide (DMF) and 3 times with isopropanol (iPrOH).

Step 4: The peptide was cleaved from the resin using 85% TFA/5% TIS/5% thioanisole and 5% phenol, followed by precipitation by dry-ice cold Et2O (Step 4).

Example 3

Synthesis of FB005CM

Step 1: The example describes the solid phase peptide synthesis of the compound on a 1 mmole scale. The following protected amino acids were sequentially added to resin: Fmoc-Lys(Aloc)-OH, Fmoc-Leu-OH, Fmoc-Leu-OH, Fmoc-Glu(tBu)-OH, Fmoc-Gln(Trt)-OH, Fmoc-Glu(tBu)-OH, Fmoc-Asn(Trt)-OH, Fmoc-Lys(Boc)-OH, Fmoc-Glu (tBu)-OH, Fmoc-Gln(Trt)-OH, Fmoc-Gln(Trt)-OH, Fmoc-Asn(Trt)-OH, Fmoc-Gln(Trt)-OH, Fmoc-Ser(tBu)-OH, Fmoc-Glu(tBu)-OH, Fmoc-Glu(tBu)-OH, Fmoc-Ile-OH, Fmoc-Leu-OH, Fmoc-Glu(tBu)-OH, Fmoc-His-OH, Fmoc- Ile-OH, Fmoc-Leu-OH, Fmoc-Glu-OH, Fmoc-Thr(tBu)-OH, Fmoc-Tyr(tBu)-OH, Fmoc-Asn(Trt)-OH, Fmoc-Asn (Trt)-OH, Fmoc-Ile-OH, Fmoc-Glu(tBu)-OH, Fmoc-Arg (tBu)-OH, Fmoc-Asp(tBu)-OH, Fmoc-Trp(Boc)-OH, Fmoc-Glu(tBu)-OH, Fmoc-Glu-OH, Fmoc-Trp(Boc)-OH, Fmoc-Thr-OH, Fmoc-Met-OH, Fmoc-Asn-OH, Fmoc-Asn-OH, Fmoc-Trp-OH, Fmoc-Ile-OH, Fmoc-Gln-OH, Fmoc-Glu-OH, Fmoc-Leu-OH, Fmoc-Ser-OH. They were dissolved in N,N-dimethylformamide (DMF) and, according to the sequence, activated using O-benzotriazol-1-yl-N,N,N',N'-tetramethyl-uronium hexafluorophosphate (HBTU) and diisopropylethylamine (DIEA). Removal of the Fmoc protecting group was achieved using a solution of 20% (V/V) piperidine in N,N-dimethylformamide (DMF) for 20 minutes (step 1). The amino group of the final amino acid was acetylated using acetic acid activated using O-benzotriazol-1-yl-N,N,N',N'-tetramethyl-uronium hexafluorophosphate (HBTU) and diisopropylethylamine (DIEA).

Step 2: The selective deprotection of the Lys (Aloc) group was performed manually and accomplished by treating the resin with a solution of 3 eq of Pd(PPh3)4 dissolved in 5 mL of C6H6CHCl3 (1:1): 2.5% NMM (v:v): 5% AcOH (v:v) for 2 h (Step 2). The resin is then washed with CHCl3 (6×5 mL), 20% AcOH in DCM (6×5 mL), DCM (6×5 mL), and DMF (6×5 mL).

Step 3: The synthesis was then re-automated for the addition of the Fmoc-AEEA-OH and the 3-maleimidopropionic acid (Step 3). Between every coupling, the resin was washed 3 times with N,N-dimethylformamide (DMF) and 3 times with isopropanol (iPrOH).

Step 4: The peptide was cleaved from the resin using 85% TFA/5% TIS/5% thioanisole and 5% phenol, followed by precipitation by dry-ice cold Et2O (Step 4).

Example 4

Synthesis of FB006

Step 1: The example describes the solid phase peptide synthesis of the compound on a 1 mmole scale. The following protected amino acids were sequentially added to resin: Fmoc-Leu-OH, Fmoc-Leu-OH, Fmoc-Glu(tBu)-OH, Fmoc-Gln(Trt)-OH, Fmoc-Glu(tBu)-OH, Fmoc-Asn(Trt)-OH, Fmoc-Lys(Boc)-OH, Fmoc-Glu(tBu)-OH, Fmoc-Gln(Trt)-OH, Fmoc-Gln(Trt)-OH, Fmoc-Asn(Trt)-OH, Fmoc-Gln (Trt)-OH, Fmoc-Ser(tBu)-OH, Fmoc-Glu(tBu)-OH, Fmoc-Glu(tBu)-OH, Fmoc-Ile-OH, Fmoc-Leu-OH, Fmoc-Glu (tBu)-OH, Fmoc-His-OH, Fmoc-Ile-OH, Fmoc-Leu-OH, Fmoc-Lys(Boc)-OH, Fmoc-Thr(tBu)-OH, Fmoc-Tyr(tBu)-OH, Fmoc-Asn(Trt)-OH, Fmoc-Asn(Trt)-OH, Fmoc-Ile-OH, Fmoc-Glu(tBu)-OH, Fmoc-Arg(Pbf)-OH, Fmoc-Asp (tBu)-OH, Fmoc-Trp(Boc)-OH, Fmoc-Glu(tBu)-OH, Fmoc-Glu(tBu)-OH, Fmoc-Trp(Boc)-OH. They were dissolved in N,N-dimethylformamide (DMF) and, according to the sequence, activated using O-benzotriazol-1-yl-N,N,N',N'-tetramethyl-uronium hexafluorophosphate (HBTU) and diisopropylethylamine (DIEA). Removal of the Fmoc protecting group was achieved using a solution of 20% (V/V) piperidine in N,N-dimethylformamide (DMF) for 20 minutes (step 1). The amino group of the final amino acid was acetylated using acetic acid activated using O-benzotriazol-1-yl-N,N,N',N'-tetramethyl-uronium hexafluorophosphate (HBTU) and diisopropylethylamine (DIEA).

Step 4: The peptide was cleaved from the resin using 85% TFA/5% TIS/5% thioanisole and 5% phenol, followed by precipitation by dry-ice cold Et2O (Step 4).

Example 5

Synthesis of FB006M

Step 1: The example describes the solid phase peptide synthesis of the compound on a 1 mmole scale. The following protected amino acids were sequentially added to resin: Fmoc-Leu-OH, Fmoc-Leu-OH, Fmoc-Glu(tBu)-OH, Fmoc-Gln(Trt)-OH, Fmoc-Glu(tBu)-OH, Fmoc-Asn(Trt)-OH, Fmoc-Lys(Boc)-OH, Fmoc-Glu(tBu)-OH, Fmoc-Gln(Trt)-OH, Fmoc-Gln(Trt)-OH, Fmoc-Asn(Trt)-OH, Fmoc-Gln (Trt)-OH, Fmoc-Ser(tBu)-OH, Fmoc-Glu(tBu)-OH, Fmoc-Glu(tBu)-OH, Fmoc-Ile-OH, Fmoc-Leu-OH, Fmoc-Glu (tBu)-OH, Fmoc-His-OH, Fmoc-Ile-OH, Fmoc-Leu-OH, Fmoc-Lys(Aloc)-OH, Fmoc-Thr(tBu)-OH, Fmoc-Tyr(tBu)-OH, Fmoc-Asn(Trt)-OH, Fmoc-Asn(Trt)-OH, Fmoc-Ile-OH, Fmoc-Glu(tBu)-OH, Fmoc-Arg(Pbf)-OH, Fmoc-Asp (tBu)-OH, Fmoc-Trp(B oc)-OH, Fmoc-Glu(tBu)-OH, Fmoc-Glu(tBu)-OH, Fmoc-Trp(Boc)-OH. They were dissolved in N,N-dimethylformamide (DMF) and, according to the sequence, activated using O-benzotriazol-1-yl-N,N,N',N'-tetramethyl-uronium hexafluorophosphate (HBTU) and diisopropylethylamine (DIEA). Removal of the Fmoc protecting group was achieved using a solution of 20% (V/V) piperidine in N,N-dimethylformamide (DMF) for 20 minutes (step 1). The amino group of the final amino acid was acetylated using acetic acid activated using O-benzotriazol-1-yl-N,N,N',N'-tetramethyl-uronium hexafluorophosphate (HBTU) and diisopropylethylamine (DIEA).

Step 2: The selective deprotection of the Lys (Aloc) group was performed manually and accomplished by treating the resin with a solution of 3 eq of Pd(PPh3)4 dissolved in 5 mL of C6H6CHCl3 (1:1): 2.5% NMM (v:v): 5% AcOH (v:v) for 2 h (Step 2). The resin is then washed with CHCl3 (6×5 mL), 20% AcOH in DCM (6×5 mL), DCM (6×5 mL), and DMF (6×5 mL).

Step 3: The synthesis was then re-automated for the addition of the Fmoc-AEEA-OH and the 3-maleimidopropionic acid (Step 3). Between every coupling, the resin was washed 3 times with N,N-dimethylformamide (DMF) and 3 times with isopropanol (iPrOH).

Step 4: The peptide was cleaved from the resin using 85% TFA/5% TIS/5% thioanisole and 5% phenol, followed by precipitation by dry-ice cold Et2O (Step 4).

Example 6

Synthesis of FB007M

Step 1: The example describes the solid phase peptide synthesis of the compound on a 1 mmole scale. The following protected amino acids were sequentially added to resin: Fmoc-Lys(Aloc)-OH, Fmoc-Leu-OH, Fmoc-Leu-OH, Fmoc-Glu(tBu)-OH, Fmoc-Gln(Trt)-OH, Fmoc-Glu(tBu)-OH, Fmoc-Asn(Trt)-OH, Fmoc-Lys(Boc)-OH, Fmoc-Glu (tBu)-OH, Fmoc-Gln(Trt)-OH, Fmoc-Gln(Trt)-OH, Fmoc-Asn(Trt)-OH, Fmoc-Gln(Trt)-OH, Fmoc-Ser(tBu)-OH, Fmoc-Glu(tBu)-OH, Fmoc-Glu(tBu)-OH, Fmoc-Ile-OH, Fmoc-Leu-OH, Fmoc-Glu(tBu)-OH, Fmoc-His-OH, Fmoc-Ile-OH, Fmoc-Leu-OH, Fmoc-Glu(tBu)-OH, Fmoc-Thr (tBu)-OH, Fmoc-Tyr(tBu)-OH, Fmoc-Asn(Trt)-OH, Fmoc-Asn(Trt)-OH, Fmoc-Ile-OH, Fmoc-Glu(tBu)-OH, Fmoc-Arg(Pbf)-OH, Fmoc-Asp(tBu)-OH, Fmoc-Trp(Boc)-OH, Fmoc-Glu(tBu)-OH, Fmoc-Glu(tBu)-OH, Fmoc-Trp(Boc)-OH. They were dissolved in N,N-dimethylformamide (DMF) and, according to the sequence, activated using O-benzotriazol-1-yl-N,N,N',N'-tetramethyluronium hexafluorophosphate (HBTU) and diisopropylethylamine (DIEA). Removal of the Fmoc protecting group was achieved using a solution of 20% (V/V) piperidine in N,N-dimethylformamide (DMF) for 20 minutes (step 1). The amino group of the final amino acid was acetylated using acetic acid activated using O-benzotriazol-1-yl-N,N,N',N'-tetramethyluronium hexafluorophosphate (HBTU) and diisopropylethylamine (DIEA).

Step 2: The selective deprotection of the Lys (Aloc) group was performed manually and accomplished by treating the resin with a solution of 3 eq of Pd(PPh3)4 dissolved in 5 mL of C6H6CHCl3 (1:1): 2.5% NMM (v:v): 5% AcOH (v:v) for 2 h (Step 2). The resin is then washed with CHCl3 (6×5 mL), 20% AcOH in DCM (6×5 mL), DCM (6×5 mL), and DMF (6×5 mL).

Step 3: The synthesis was then re-automated for the addition of the Fmoc-AEEA-OH and the 3-maleimidopropionic acid (Step 3). Between every coupling, the resin was washed 3 times with N,N-dimethylformamide (DMF) and 3 times with isopropanol (iPrOH).

Step 4: The peptide was cleaved from the resin using 85% TFA/5% TIS/5% thioanisole and 5% phenol, followed by precipitation by dry-ice cold Et2O (Step 4).

Example 7

Synthesis of FB010M

Step 1: The example describes the solid phase peptide synthesis of the compound on a 1 mmole scale. The following protected amino acids were sequentially added to resin: Fmoc-Phe-OH, Fmoc-Trp(Boc)-OH, Fmoc-Glu(tBu)-OH, Fmoc-Trp(Boc)-OH, Fmoc-Leu-OH, Fmoc-Ser(tBu)-OH, Fmoc-Ala-OH, Fmoc-Trp(Boc)-OH, Fmoc-Lys(Boc)-OH, Fmoc-Asp(tBu)-OH, Fmoc-Leu-OH, Fmoc-Lys(Boc)-OH, Fmoc-Gln(Trt)-OH, Fmoc-Leu-OH, Fmoc-Glu(tBu)-OH, Fmoc-Tyr(tBu)-OH, Fmoc-Glu(tBu)-OH, Fmoc-Asn(Trt)-OH, Fmoc-Lys(Boc)-OH, Fmoc-Glu(tBu)-OH, Fmoc-Gln (Trt)-OH, Fmoc-Gln(Trt)-OH, Fmoc-Ile-OH, Fmoc-Gln (Trt)-OH, Fmoc-Ala-OH, Fmoc-Gln(Trt)-OH, Fmoc-Lys (Aloc)-OH, Fmoc-Leu-OH, Fmoc-Leu-OH, Fmoc-Ala-OH, Fmoc-Thr(tBu)-OH, Fmoc-Ile-OH, Fmoc-Lys(Boc)-OH, Fmoc-Gln(Trt)-OH, Fmoc-Glu(tBu)-OH, Fmoc-Trp(Boc)-OH, Fmoc-Glu(tBu)-OH, Fmoc-Gln(Trt)-OH, Fmoc-Trp (Boc)-OH. They were dissolved in N,N-dimethylformamide (DMF) and, according to the sequence, activated using O-benzotriazol-1-yl-N,N,N',N'-tetramethyl-uronium hexafluorophosphate (HBTU) and diisopropylethylamine (DIEA). Removal of the Fmoc protecting group was achieved using a solution of 20% (V/V) piperidine in N,N-dimethylformamide (DMF) for 20 minutes (step 1). The amino group of the final amino acid was acetylated using acetic acid activated using O-benzotriazol-1-yl-N,N,N',N'-tetramethyluronium hexafluorophosphate (HBTU) and diisopropylethylamine (DIEA).

Step 2: The selective deprotection of the Lys (Aloc) group was performed manually and accomplished by treating the resin with a solution of 3 eq of Pd(PPh3)4 dissolved in 5 mL of C6H6CHCl3 (1:1): 2.5% NMM (v:v): 5% AcOH (v:v) for 2 h (Step 2). The resin is then washed with CHCl3 (6×5 mL), 20% AcOH in DCM (6×5 mL), DCM (6×5 mL), and DMF (6×5 mL).

Step 3: The synthesis was then re-automated for the addition of the Fmoc-AEEA-OH and the 3-maleimidopropionic acid (Step 3). Between every coupling, the resin was washed 3 times with N,N-dimethylformamide (DMF) and 3 times with isopropanol (iPrOH).

Step 4: The peptide was cleaved from the resin using 85% TFA/5% TIS/5% thioanisole and 5% phenol, followed by precipitation by dry-ice cold Et2O (Step 4).

Example 8

Synthesis of FB010KM

Step 1: The example describes the solid phase peptide synthesis of the compound on a 1 mmole scale. The following protected amino acids were sequentially added to resin: Fmoc-Lys(Aloc)-OH, Fmoc-Phe-OH, Fmoc-Trp(Boc)-OH, Fmoc-Glu(tBu)-OH, Fmoc-Trp(Boc)-OH, Fmoc-Leu-OH, Fmoc-Ser(tBu)-OH, Fmoc-Ala-OH, Fmoc-Trp(Boc)-OH, Fmoc-Lys(Boc)-OH, Fmoc-Asp(tBu)-OH, Fmoc-Leu-OH, Fmoc-Lys(Boc)-OH, Fmoc-Gln(Trt)-OH, Fmoc-Leu-OH, Fmoc-Glu(tBu)-OH, Fmoc-Tyr(tBu)-OH, Fmoc-Glu(tBu)-OH, Fmoc-Asn(Trt)-OH, Fmoc-Lys(Boc)-OH, Fmoc-Glu (tBu)-OH, Fmoc-Gln(Trt)-OH, Fmoc-Gln(Trt)-OH, Fmoc-Ile-OH, Fmoc-Gln(Trt)-OH, Fmoc-Ala-OH, Fmoc-Gln(Trt)-OH, Fmoc-Glu(tBu)-OH, Fmoc-Ile-OH, Fmoc-Leu-OH, Fmoc-Ala-OH, Fmoc-Thr(tBu)-OH, Fmoc-Ile-OH, Fmoc-Lys(Boc)-OH, Fmoc-Gln(Trt)-OH, Fmoc-Glu(tBu)-OH, Fmoc-Trp(Boc)-OH, Fmoc-Glu(tBu)-OH, Fmoc-Gln(Trt)-OH, Fmoc-Trp(Boc)-OH. They were dissolved in N,N-dimethylformamide (DMF) and, according to the sequence, activated using O-benzotriazol-1-yl-N,N,N',N'-tetramethyl-uronium hexafluorophosphate (HBTU) and diisopropylethylamine (DIEA). Removal of the Fmoc protecting group was achieved using a solution of 20% (V/V) piperidine in N,N-dimethylformamide (DMF) for 20 minutes (step 1). The amino group of the final amino acid was acetylated using acetic acid activated using O-benzotriazol-1-yl-N,N,N',N'-tetramethyluronium hexafluorophosphate (HBTU) and diisopropylethylamine (DIEA).

Step 2: The selective deprotection of the Lys (Aloc) group was performed manually and accomplished by treating the resin with a solution of 3 eq of Pd(PPh3)4 dissolved in 5 mL of C6H6CHCl3 (1:1): 2.5% NMM (v:v): 5% AcOH (v:v) for 2 h (Step 2). The resin is then washed with CHCl3 (6×5 mL), 20% AcOH in DCM (6×5 mL), DCM (6×5 mL), and DMF (6×5 mL).

Step 3: The synthesis was then re-automated for the addition of the Fmoc-AEEA-OH and the 3-maleimidopropionic acid (Step 3). Between every coupling, the resin was washed 3 times with N,N-dimethylformamide (DMF) and 3 times with isopropanol (iPrOH).

Step 4: The peptide was cleaved from the resin using 85% TFA/5% TIS/5% thioanisole and 5% phenol, followed by precipitation by dry-ice cold Et2O (Step 4).

Example 9

Viral Inhibition by Modified Peptides

The antiviral activity and cytotoxicity of FB005, FB006, FB006M, FB007M, FB010KM, and FM010M were tested against HIV-$1_{IIIB}$ in fresh human PBMC cultures. The four modified peptides FB006M, FB007M, FB010M, and FB010KM were conjugated to human serum albumin (HSA) by mixing prior to the antiviral test. The results appear in Table 8 below, where $IC_{50}$ value is the 50% viral inhibition drug concentration, and $TC_{50}$ value is the 50% cytotoxicity drug concentration.

Cellular Anti-HIV Assay

Pretitered aliquots of HIV-$1_{IIIB}$ was removed from the freezer (−80° C.) and thawed rapidly to room temperature in a biological safety cabinet immediately before use.

Fresh human PBMCs were isolated from screened donors, seronegative for HIV and HBV (Interstate Blood Bank, Inc.; Memphis, Tenn.). Cells were pelleted/washed 2-3 times by low speed centrifugation and resuspension in PBS to remove contaminating platelets. The Leukophoresed blood was then diluted 1:1 with Dulbecco's phosphate buffered saline (PBS) and layered over 14 mL of Lymphocyte Separation Medium in a 50 mL centrifuge tube and then centrifuged for 30 minutes at 600×g. Banded PBMCs were gently aspirated from the resulting interface and subsequently washed 2× with PBS by low speed centrifugation. After the final wash, cells were enumerated by trypan blue exclusion and re-suspended at $1\times10^7$ cells/mL in RPMI 1640 supplemented with 15% Fetal Bovine Serum (FBS), 2 mM L-glutamine, 4 μg/mL Phytohemagglutinin (PHA-P, Sigma). The cells were allowed to incubate for 48-72 hours at 37° C. After incubation, PBMCs were centrifuged and resuspended in RPMI 1640 with 15% FBS, 2 mM L-glutamine, 100 U/mL penicillin, 100 μg/mL streptomycin, 10 μg/mL gentamycin, and 20 U/mL recombinant human IL-2 (R&D Systems, Inc). PBMCs were maintained in this medium at a concentration of $1\text{-}2\times10^6$ cells/mL with biweekly medium changes until used in the assay protocol. Cells were kept in culture for a maximum of two weeks before being deemed too old for use in assays and discarded. Monocytes were depleted from the culture as the result of adherence to the tissue culture flask.

For the standard PBMC assay, PHA-P stimulated cells from at least two normal donors were pooled, diluted in fresh medium to a final concentration of $1\times10^6$ cells/mL, and plated in the interior wells of a 96 well round bottom microplate at 50 μL/well ($5\times10^4$ cells/well). Each plate contains virus/cell control wells (cells plus virus), experimental wells (drug plus cells plus virus) and compound control wells (drug plus media without cells, necessary for MTS monitoring of cytotoxicity). Since HIV-1 is not cytopathic to PBMCs, this allows the use of the same assay plate for both antiviral activity and cytotoxicity measurements. Test drug dilutions were prepared at a 2× concentration in microtiter tubes and 100 μL of each concentration was placed in appropriate wells using the standard format. 50 μL of a predetermined dilution of virus stock was placed in each test well (final MOI≈0.1). The PBMC cultures were maintained for seven days following infection at 37° C., 5% $CO_2$, after which cell-free supernatant samples were collected for analysis of reverse transcriptase activity and/or HIV p24 content. Following removal of supernatant samples, compound cytotoxicity was measured by addition of MTS to the plates for determination of cell viability. Wells were also examined microscopically and any abnormalities noted.

Secondary Cytotoxicity Assay

In order to test the cytotoxicity of the compounds at higher concentrations than those used in the anti-HIV efficacy evaluation, a secondary assay was used. This assay was essentially the same as described above for the anti-HIV efficacy evaluation, however no virus was added to the wells (replaced by media without virus) and the high-test concentration was increased to 25 μM. Following incubation, plates were assayed for cell viability using MTS as described below.

TABLE 8

| Compound | Comment | $IC_{50}$ (nM) | $TC_{50}$ (nM) |
|---|---|---|---|
| FB005 | Unmodified peptide | 0.93 | 14,300 |
| FB006 | Unmodified peptide | 1.41 | 15,900 |
| FB006M | modified peptide conjugated with HSA | 3.94 | >25,000 |
| FB007M | modified peptide conjugated with HSA | 9.09 | >25,000 |
| FB010M | modified peptide conjugated with HSA | 7.78 | >25,000 |
| FB010KM | modified peptide conjugated with HSA | 15.7 | >25,000 |

Although the foregoing invention has been described in some detail by way of illustration and example for purposes of clarity of understanding, it will be obvious that certain changes and modifications may be practiced within the scope of the appended claims. Modifications of the above-described modes for carrying out the invention that are obvious to persons of skill in medicine, immunology, virology, pharmacology, protein synthesis and modification and/or related fields are intended to be within the scope of the following claims.

All publications and patent applications mentioned in this specification are indicative of the level of skill of those skilled in the art to which this invention pertains. All such publications and patent applications are herein incorporated by reference to the same extent as if each individual publication or patent application was specifically and individually indicated to be incorporated by reference.

Certain peptides and derivatives thereof that are useful in preventing and/or treating viral infection, particularly HIV infection, were disclosed in U.S. Provisional Patent Application No. 60/412,797, filed Sep. 24, 2002, the contents of which (including any sequences contained therein) is herein incorporated by reference in its entirety.

What is claimed is:

1. An isolated FB005, FB006 or FB066 peptide comprising the sequence of SEQ ID NO:1, SEQ ID NO:2 or SEQ ID NO: 7, respectively.

2. An isolated peptide derivatized with a maleimide linking moiety, selected from the group consisting of:

(a) the FB005M peptide of SEQ ID NO:8;

(b) the FB005CM peptide of SEQ ID NO:9;

(c) the FB006M peptide of SEQ ID NO:10;

(d) the FB007M peptide of SEQ ID NO:11;

(e) the FB066M peptide of SEQ ID NO:14; and (f) the FB066KM peptide of SEQ ID NO:15.

3. An isolated, derivatized peptide selected from the group consisting of:

(a) SEQ ID NO:1;

(b) SEQ ID NO:2; and (c) SEQ ID NO:7, wherein predetermined amino acid residues in the peptide sequence are derivatized by conjugating a coupling group to said predetermined amino acid residues.

* * * * *

SEQUENCE LISTING

<160> NUMBER OF SEQ ID NOS: 15

<210> SEQ ID NO 1
<211> LENGTH: 44
<212> TYPE: PRT
<213> ORGANISM: Artificial sequence
<220> FEATURE:
<223> OTHER INFORMATION: Synthetic Construct

<400> SEQUENCE: 1

Ser Leu Glu Gln Ile Trp Asn Asn Met Thr Trp Glu Glu Trp Asp Arg

-continued

```
1               5                   10                  15

Glu Ile Asn Asn Tyr Thr Glu Leu Ile His Glu Leu Ile Glu Glu Ser
            20                  25                  30

Gln Asn Gln Gln Glu Lys Asn Glu Gln Glu Leu Leu
        35                  40


<210> SEQ ID NO 2
<211> LENGTH: 34
<212> TYPE: PRT
<213> ORGANISM: Artificial sequence
<220> FEATURE:
<223> OTHER INFORMATION: Synthetic Construct

<400> SEQUENCE: 2

Trp Glu Glu Trp Asp Arg Glu Ile Asn Asn Tyr Thr Lys Leu Ile His
1               5                   10                  15

Glu Leu Ile Glu Glu Ser Gln Asn Gln Gln Glu Lys Asn Glu Gln Glu
            20                  25                  30

Leu Leu


<210> SEQ ID NO 3
<211> LENGTH: 39
<212> TYPE: PRT
<213> ORGANISM: Artificial sequence
<220> FEATURE:
<223> OTHER INFORMATION: Synthetic Construct

<400> SEQUENCE: 3

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Glu Trp Phe
        35


<210> SEQ ID NO 4
<211> LENGTH: 36
<212> TYPE: PRT
<213> ORGANISM: Artificial sequence
<220> FEATURE:
<223> OTHER INFORMATION: Synthetic Construct

<400> SEQUENCE: 4

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35


<210> SEQ ID NO 5
<211> LENGTH: 34
<212> TYPE: PRT
<213> ORGANISM: Artificial sequence
<220> FEATURE:
<223> OTHER INFORMATION: Synthetic Construct

<400> SEQUENCE: 5

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30
```

-continued

Leu Leu

<210> SEQ ID NO 6
<211> LENGTH: 34
<212> TYPE: PRT
<213> ORGANISM: Artificial sequence
<220> FEATURE:
<223> OTHER INFORMATION: Synthetic Construct

<400> SEQUENCE: 6

Trp Gln Glu Trp Glu Arg Lys Val Asp Phe Leu Glu Glu Asn Ile Thr
1               5                   10                  15

Ala Leu Leu Glu Glu Ala Gln Ile Gln Gln Glu Lys Asn Met Tyr Glu
            20                  25                  30

Leu Gln

<210> SEQ ID NO 7
<211> LENGTH: 34
<212> TYPE: PRT
<213> ORGANISM: Artificial sequence
<220> FEATURE:
<223> OTHER INFORMATION: Synthetic Construct

<400> SEQUENCE: 7

Trp Glu Glu Trp Asp Arg Glu Ile Asn Asn Tyr Thr Lys Leu Ile His
1               5                   10                  15

Glu Leu Ile Glu Glu Ser Gln Asn Gln Gln Glu Glu Asn Glu Gln Glu
            20                  25                  30

Leu Leu

<210> SEQ ID NO 8
<211> LENGTH: 44
<212> TYPE: PRT
<213> ORGANISM: Artificial sequence
<220> FEATURE:
<223> OTHER INFORMATION: Synthetic Construct
<220> FEATURE:
<221> NAME/KEY: MISC_FEATURE
<222> LOCATION: (23)..(23)
<223> OTHER INFORMATION: Xaa represents a Lysine residue derivatized
      with a maleimide moiety.

<400> SEQUENCE: 8

Ser Leu Glu Gln Ile Trp Asn Asn Met Thr Trp Glu Glu Trp Asp Arg
1               5                   10                  15

Glu Ile Asn Asn Tyr Thr Xaa Leu Ile His Glu Leu Ile Glu Glu Ser
            20                  25                  30

Gln Asn Gln Gln Glu Lys Asn Glu Gln Glu Leu Leu
        35                  40

<210> SEQ ID NO 9
<211> LENGTH: 45
<212> TYPE: PRT
<213> ORGANISM: Artificial sequence
<220> FEATURE:
<223> OTHER INFORMATION: Synthetic Construct
<220> FEATURE:
<221> NAME/KEY: MISC_FEATURE
<222> LOCATION: (45)..(45)
<223> OTHER INFORMATION: Xaa represents a Lysine residue derivatized
      with a maleimide moiety.

<400> SEQUENCE: 9

Ser Leu Glu Gln Ile Trp Asn Asn Met Thr Trp Glu Glu Trp Asp Arg

-continued

```
1               5                   10                  15

Glu Ile Asn Asn Tyr Thr Glu Leu Ile His Glu Leu Ile Glu Glu Ser
            20                  25                  30

Gln Asn Gln Gln Glu Lys Asn Glu Gln Glu Leu Leu Xaa
        35                  40                  45


<210> SEQ ID NO 10
<211> LENGTH: 34
<212> TYPE: PRT
<213> ORGANISM: Artificial sequence
<220> FEATURE:
<223> OTHER INFORMATION: Synthetic Construct
<220> FEATURE:
<221> NAME/KEY: MISC_FEATURE
<222> LOCATION: (13)..(13)
<223> OTHER INFORMATION: Xaa represents a Lysine residue derivatized
      with a maleimide moiety.

<400> SEQUENCE: 10

Trp Glu Glu Trp Asp Arg Glu Ile Asn Asn Tyr Thr Xaa Leu Ile His
1               5                   10                  15

Glu Leu Ile Glu Glu Ser Gln Asn Gln Gln Glu Lys Asn Glu Trp Glu
            20                  25                  30

Leu Leu


<210> SEQ ID NO 11
<211> LENGTH: 35
<212> TYPE: PRT
<213> ORGANISM: Artificial sequence
<220> FEATURE:
<223> OTHER INFORMATION: Synthetic Construct
<220> FEATURE:
<221> NAME/KEY: MISC_FEATURE
<222> LOCATION: (35)..(35)
<223> OTHER INFORMATION: Xaa represents a Lysine residue derivatized
      with a maleimide moiety.

<400> SEQUENCE: 11

Trp Glu Glu Trp Asp Arg Glu Ile Asn Asn Tyr Thr Glu Leu Ile His
1               5                   10                  15

Glu Leu Ile Glu Glu Ser Gln Asn Gln Gln Glu Lys Asn Glu Gln Glu
            20                  25                  30

Leu Leu Xaa
        35


<210> SEQ ID NO 12
<211> LENGTH: 39
<212> TYPE: PRT
<213> ORGANISM: Artificial sequence
<220> FEATURE:
<223> OTHER INFORMATION: Synthetic Construct
<220> FEATURE:
<221> NAME/KEY: MISC_FEATURE
<222> LOCATION: (13)..(13)
<223> OTHER INFORMATION: Xaa represents a Lysine residue derivatized
      with a maleimide moiety.

<400> SEQUENCE: 12

Trp Gln Glu Trp Glu Gln Lys Ile Thr Ala Leu Leu Xaa Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Glu Trp Phe
        35
```

-continued

```
<210> SEQ ID NO 13
<211> LENGTH: 40
<212> TYPE: PRT
<213> ORGANISM: Artificial sequence
<220> FEATURE:
<223> OTHER INFORMATION: Synthetic Construct
<220> FEATURE:
<221> NAME/KEY: MISC_FEATURE
<222> LOCATION: (40)..(40)
<223> OTHER INFORMATION: Xaa represents a Lysine residue derivatized
      with a maleimide moiety.

<400> SEQUENCE: 13

Trp Gln Glu Trp Glu Gln Lys Ile Thr Ala Leu Ile Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Glu Trp Phe Xaa
        35                  40


<210> SEQ ID NO 14
<211> LENGTH: 34
<212> TYPE: PRT
<213> ORGANISM: Artificial sequence
<220> FEATURE:
<223> OTHER INFORMATION: Synthetic Construct
<220> FEATURE:
<221> NAME/KEY: MISC_FEATURE
<222> LOCATION: (13)..(13)
<223> OTHER INFORMATION: Xaa represents a Lysine residue derivatized
      with a maleimide moiety.

<400> SEQUENCE: 14

Trp Glu Glu Trp Asp Arg Glu Ile Asn Asn Tyr Thr Xaa Leu Ile His
1               5                   10                  15

Glu Leu Ile Glu Glu Ser Gln Asn Gln Gln Glu Glu Asn Glu Gln Glu
            20                  25                  30

Leu Leu


<210> SEQ ID NO 15
<211> LENGTH: 35
<212> TYPE: PRT
<213> ORGANISM: Artificial sequence
<220> FEATURE:
<223> OTHER INFORMATION: Synthetic Construct
<220> FEATURE:
<221> NAME/KEY: MISC_FEATURE
<222> LOCATION: (35)..(35)
<223> OTHER INFORMATION: Xaa represents a Lysine residue derivatized
      with a maleimide moiety.

<400> SEQUENCE: 15

Trp Glu Glu Trp Asp Arg Glu Ile Asn Asn Tyr Thr Lys Leu Ile His
1               5                   10                  15

Glu Leu Ile Glu Glu Ser Gln Asn Gln Gln Glu Glu Asn Glu Gln Glu
            20                  25                  30

Leu Leu Xaa
        35
```